(12) United States Patent
Bonnert et al.

(10) Patent No.: US 7,687,535 B2
(45) Date of Patent: Mar. 30, 2010

(54) SUBSTITUTED 3-SULFUR INDOLES

(75) Inventors: Roger Bonnert, Loughborough (GB); Rukhsana Mohammed, Muscat (GB); Mark Robert Dickinson, Loughborough (GB)

(73) Assignee: AstraZeneca AB (SE)

( * ) Notice: Subject to any disclaimer, the term of this patent is extended or adjusted under 35 U.S.C. 154(b) by 847 days.

(21) Appl. No.: 10/558,228

(22) PCT Filed: May 25, 2004

(86) PCT No.: PCT/SE2004/000808

§ 371 (c)(1),
(2), (4) Date: Nov. 22, 2005

(87) PCT Pub. No.: WO2004/106302

PCT Pub. Date: Dec. 9, 2004

(65) Prior Publication Data

US 2008/0249110 A1    Oct. 9, 2008

(30) Foreign Application Priority Data

May 27, 2003   (SE) .................................. 0301569
Aug. 27, 2003   (SE) .................................. 0302305

(51) Int. Cl.
*A61K 31/405* (2006.01)
*C07D 209/04* (2006.01)
(52) U.S. Cl. ....................... 514/418; 548/484
(58) Field of Classification Search ................ 548/400, 548/416, 452, 469, 484; 514/418
See application file for complete search history.

(56) References Cited

U.S. PATENT DOCUMENTS

| 5,459,150 | A  | 10/1995 | Brooks et al. |
| 5,486,525 | A  | 1/1996  | Summers, Jr. et al. |
| 5,567,711 | A  | 10/1996 | Shepard et al. |
| 6,916,841 | B2 | 7/2005  | Seehra et al. |
| 6,933,316 | B2 | 8/2005  | Hsieh et al. |
| 7,166,607 | B2 | 1/2007  | Bonnert et al. |
| 2005/0222201 | A1 | 10/2005 | Birkinshaw et al. |
| 2006/0111426 | A1 | 5/2006  | Bonnert et al. |
| 2006/0264444 | A1 | 11/2006 | Bonnert et al. |
| 2008/0027092 | A1 | 1/2008  | Bonnert et al. |
| 2008/0051586 | A1 | 2/2008  | Keegan et al. |
| 2008/0249110 | A1 | 10/2008 | Bonnert et al. |
| 2009/0143449 | A1 | 6/2009  | Bonnert et al. |

FOREIGN PATENT DOCUMENTS

| EP | 0254241 | 1/1988 |
| EP | 0530907 A1 | 3/1993 |
| EP | 0576347 A1 | 12/1993 |
| EP | 0924209 B1 | 6/1999 |
| EP | 1170594 A2 | 1/2002 |
| EP | 1505061 | 2/2005 |
| GB | 1356834 | 6/1974 |
| GB | 2422831 | 8/2006 |
| WO | WO94/19321 | 9/1994 |
| WO | WO95/16687 | 6/1995 |
| WO | WO98/13368 | 4/1998 |
| WO | WO99/09007 | 2/1999 |
| WO | WO00/78761 A1 | 12/2000 |
| WO | WO 01/32621 | * 5/2001 | ................ 548/469 |
| WO | WO01/47922 A2 | 7/2001 |
| WO | WO01/92224 A1 | 12/2001 |
| WO | WO03/064387 A2 | 8/2003 |
| WO | WO 03/066046 | 8/2003 |
| WO | WO 03/066047 | 8/2003 |
| WO | WO03/097598 | 11/2003 |
| WO | WO 03/101961 A1 | 12/2003 |
| WO | WO 03/101981 | 12/2003 |
| WO | WO 2004/007451 A1 | 1/2004 |
| WO | WO 2004/016609 | 2/2004 |
| WO | WO 2004/106302 | 12/2004 |
| WO | WO 2005/019171 | 3/2005 |
| WO | WO 2005/040114 | 5/2005 |
| WO | WO 2005/054232 | 6/2005 |
| WO | WO 2006/075139 | 7/2006 |
| WO | WO 2007/138282 | 12/2007 |
| WO | WO 2007/140786 | 12/2007 |
| WO | WO 2008/000409 | 1/2008 |

OTHER PUBLICATIONS

[Patani, George A. Bioisosterism: A rational appraoch in drug design. Chem. Rev. 96 (1996) 3147-3176.].*
Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001):3-26.*
Atkinson et al., "A New synthesis of 3-Arylthioindoles", *Synthesis* 6:480-481 (1988).
Cecil Textbook of Medicine, 20th edition, vol. 2:1992-1996 (1996).
Cecil Textbook of Medicine, 20$^{th}$ edition, vol. 2:2050-2057 (1996).
FDA mulls drug to slow late-stage Alzheimer's [online], [retrieved on Sep. 23, 2003]. Retrieved from the Internet, URL:http://www.cnn.com/2003/HEALTH/conditions/09/24/alzheimers.drug.ap/indexhtml>.
Database CA 'Online! Chemical Abstracts Service, Columbus, Ohio, US; Tanimoto, Norihiko et al: "Preparation of indole derivatives as PGD2 receptor antagonists" XP002301963 retrieved from STN Database accession No. 2003:931327.
Garcia et al., "A Novel Synthesis of 3-Cyanoindoles and a New Route to Indole-3-Carboxylic Acid Derivatives", *Tetrahedron Letters* 26(15):1827-1830 (1985).

(Continued)

*Primary Examiner*—Kamal A Saeed
*Assistant Examiner*—Samantha L Shterengarts
(74) *Attorney, Agent, or Firm*—Fish & Richardson P.C.

(57) ABSTRACT

The present invention relates to substituted indoles useful as pharmaceutical compounds for treating respiratory disorders.

7 Claims, No Drawings

OTHER PUBLICATIONS

Hamel et al., "Regioselective Synthesis of Mixed Indole 2,3-Bis-(sulfides). A Study of the Mechanism of the Second Sulfenylation of Indole", *J. Org. Chem.* 61:1573-1577 (1996).

Hary et al., "Efficient synthesis of 3-(4,5-dihydro-1H-imidazole-2-yl)-1H-indoles", *Tetrahedron Letters* 42:5187-5189 (2001).

Howard et al., "Synthesis and aldose reductase inhibitory activity of substituted 2(1H)- benzimidazolone- and oxindole-1-acetic acids", *Eur J Med Chem* 27:779-789 (1992).

Lüscher et al., "Deblocking of o-Nitrophenylsulfenyl-Protected Peptides by Ammonium Thiocyanate and (2-Methyl-1-indolyl) acetic acid", *Helv. Chim. Acta* 66(2):602-605 (1983).

Matassa et al., "Evolution of a Series of Peptidoleukotriene Antagonists: Synthesis and Structure/Activity Relationships of 1,3,5-Substituted Indoles and Indazoles", *J. Med. Chem.* 33:1781-1790 (1990).

Matsugi et al., "An efficient sylfenylation of aromatics using highly active quinone mono O,S-acetal bearing a pentafluorophenylthio group", *Tetrahedron Letters* 42:1077-1080 (2001).

Matsugi et al., "Facile and Efficient Sulfenylation Method Using Quinone Mono-O,S-Acetals under Mild Conditions", *J. Org. Chem.* 66:2434-2441 (2001).

Ovenden et al., "Echinosulfonic Acids A-C and Echinosulfone A: Novel Bromoindole Sulfonic Acids and a Sulfone from a Southern Australian Marine Sponge, *Echinodictyum*", *J. Nat. Prod.* 62:1246-1249 (1999).

STN International, Caplus accession No. 1977:535057, Document No. 87:135057, Sankyo Co., Ltd., "3-Indolyl thio ethers", & JP,A2,52039671, 19770328, RN 64137-76-4, 54491-43-9, 56366-45-1.

STN International, Caplus accession No. 1980:6356, Document No. 92:6356, Gabrielyan, G.E. et al.: "Indole derivatives. LX. Synthesis of indole compounds with a furan ring", & Armyanskii Khimicheskii Zhurnal (1979), 32(4), 309-14, RN 51842-57-0.

STN International, Caplus accession No. 2001:235566, Document No. 134:266203, Kato, Susumu et al.: "Preparation and application of benzopyranone derivatives"; & JP,A2,2001089471, 20010403, RN 332082-10-7.

STN International, Chemcats accession No. 2000:1027702, Apr. 26, 2001, 8004-3013, "1H-Indole-1-acetic acid, 2-methyl-3-(phenylthio)-, ethyl esther", CAS Registry No. 300860-50-8.

STN International, file Caplus, Capus accession No. 1995:401159, Document No. 122:187576, Yoshitomi Pharmaceutical Industries, Ltd., "Preparation of fused pyrazole derivatives", & JP,A2, 06206872, 19940726.

STN International, File Caplus, Caplus accession 2001:338492, Document No. 134:353315, Wakunaga Pharmaceutical Co., Ltd.: "Preparation of indole derivatives as chymase inhibitors and drugs containing the same as the active ingredient", & WO,A1,2001032621, 20010510.

"COPD: Causes and Prevention." NIH SeniorHealth. National Heart, Lung, and Blood Institute. Accessed Apr. 6, 2009. <http://nihseniorhealth.gov/copd/causesandprevention/01.html>.

"Prevention of Cystic Fibrosis." WrongDiagnosis.com. Accessed Apr. 6, 2009. <http://www.wrongdiagnosis.com/c/cf/prevent.htm>.

* cited by examiner

SUBSTITUTED 3-SULFUR INDOLES

CROSS-REFERENCE TO RELATED APPLICATIONS

This application is a national phase application under 35 U.S.C. §371 of PCT International Application No. PCT/SE2004/000808, filed May 25, 2004, which claims priority to Swedish Application Serial No. 0301569-0, filed May 27, 2003 and Swedish Application Serial No. 0302305-8, filed Aug. 27, 2003.

The present invention relates to substituted indoles useful as pharmaceutical compounds for treating respiratory disorders, pharmaceutical compositions containing them, and processes for their preparation.

EPA 1 170 594 discloses methods for the identification of compounds useful for the treatment of disease states mediated by prostaglandin D2, a ligand for orphan receptor CRTh2. U.S. Pat. No. 5,486,525 discloses a series of indoles said to possess PAF antagonist activity. It has now surprisingly been found that certain indole acetic acids are active at the CRTh2 receptor, and as a consequence are expected to be potentially useful for the treatment of various respiratory diseases, including asthma and COPD.

In a first aspect the invention therefore provides a compound of formula (I) or a pharmaceutically acceptable salt and solvates thereof:

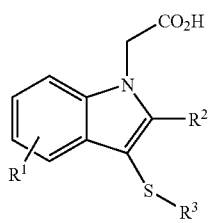

(I)

in which:

$R^1$ is one or more substituents independently selected from $NR^4SO_2R^5$, $NR^4CO_2R^6$, $NR^4COR^6$, $NR^4SO_2NR^5R^6$, $NHSO_2R^5$, $NHCO_2R^6$, $NHCOR^6$, $NHCONR^4$, $NHSO_2NR^5R^6$, or heteroaryl, the latter which may be optionally substituted by halogen, CN, $OR^7$, $C_{1-3}$ alkyl (which may be optionally substituted by halogen atoms);

$R^2$ is hydrogen, halogen, CN, $SO_2R^4$ or $CONR^5R^6$, $CH_2OH$, $CH_2OR^4$ or $C_{1-7}$alkyl, the latter group being optionally substituted by one or more substituents independently selected from halogen atoms, $OR^8$ and $NR^5R^6$, $S(O)_xR^7$ where x is 0, 1 or 2;

$R^3$ is aryl or heteroaryl each of which is optionally substituted by one or more substituents independently selected from hydrogen, halogen, CN, OH, $SO_2^4$, $OR^4$, $SR^4$, $SOR^4$, $SO_2NR^5R^6$, $CONR^5R^6$, $NR^5R^6$, $NHSO_2R^4$, $NHCOR^4$, $NHCO_2^4$, $NR^7SO_2R^4$, $NR^7CO_2R^4$, $NR^7COR^4$, $C_2$-$C_6$ alkenyl, $C_2$-$C_6$ alynyl, $C_{1-6}$ alkyl, the latter three groups being optionally substituted by one or more substituents independently selected from halogen atoms, $OR^8$ and $NR^5R^6$, $S(O)_x R^7$ where x is 0, 1 or 2;

$R^4$ represents aryl, heteroaryl, or $C_{1-6}$alkyl all of which may be optionally substituted by one or more substituents independently selected from halogen atoms, aryl, heteroaryl, $OR^{10}$, OH, $NR^{11}R^{12}$, $S(O)_xR^{13}$ (where x is 0,1 or 2), $CONR^{14}R^{15}$, $NR^{14}COR^{15}$, $SO_2NR^{14}R^{15}$, $NR^{14}SO_2R^{15}$, CN, nitro;

$R^5$ and $R^6$ independently represent a hydrogen atom, a $C_{1-6}$ alkyl group, or an aryl, or a heteroaryl, the latter three of which may be optionally substituted by one or more substituents independently selected from halogen atoms, aryl, $OR^8$ and $NR^{14}R^{15}$, $CONR^{14}R^{15}$, $NR^{14}COR^{15}$, $SO_2NR^{14}R^{15}$, $NR^{14}SO_2R^{15}$; CN, nitro, $C_{1-3}$ alkyl (which may be optionally substituted by halogen atoms;

or $R^5$ and $R^6$ together with the nitrogen atom to which they are attached can form a 3-8 membered saturated heterocylic ring optionally containing one or more atoms selected from O, $S(O)_x$ where x is 0, 1 or 2, $NR^{16}$, and itself optionally substituted by $C_{1-3}$ alkyl;

$R^7$ and $R^{13}$ independently represent a $C_1$-$C_6$, alkyl, an aryl or a heteroaryl group, all of which may be optionally substituted by halogen atoms;

$R^8$ represents a hydrogen atom, $C(O)R^9$, $C_1$-$C_6$ alkyl (optionally substituted by halogen atoms or aryl) an aryl or a heteroaryl group (optionally substituted by halogen);

each of $R^9$, $R^{10}$, $R^{11}$, $R^{12}$, $R^{14}$, $R^{15}$, independently represents a hydrogen atom, $C_1$-$C_6$ alkyl, an aryl or a heteroaryl group (all of which may be optionally substituted by halogen atoms); and $R^{16}$ is hydrogen, $C_{1-4}$ alkyl, $COC_1$-$C_4$ alkyl or $COYC_1$-$C_4$alkyl where Y is O or $NR^7$.

In the context of the present specification, unless otherwise indicated, an alkyl or alkenyl group or an alkyl or alkenyl moiety in a substituent group may be linear, branched or cyclic.

Aryl groups as defined herein can be phenyl or naphthyl.

Heteroaryl is defined as a 5-7 membered aromatic ring or can be 6,6- or 6,5-fused bicyclic. each ring containing one or more heteroatoms selected from N, S and O. Examples include pyridine, pyrimidine, thiazole, oxazole, pyrazole, imidazole, furan, isoxazole, pyrrole, isothiazole and azulene, naphthyl, indene, quinoline, isoquinoline, indole, indolizine, benzo[b]furan, benzo[b]thiophene, 1H-indazole, benzimidazole, benzthiazole, benzoxazole, purine, 4H-quinolizine, cinnoline, phthalazine, quinazoline, quinoxaline, 1,8-naphthyridine, pteridine, quinolone.

When $R^5$ and $R^6$ together with the nitrogen atom to which they are attached can form a 3-8 membered saturated heterocylic ring, examples include morpholine, thiomorpholine, azetidine, imidazolidine, pyrrolidine, piperidine and piperazine. Substituents can be present on carbon or appropriate nitrogen atoms of such rings.

Suitably $R^1$ is one or more substituents independently selected from $NR^4SO_2R^5$, $NR^4CO_2R^6$, $NR^4COR^6$, $NR^4SO_2NR^5R^6$, $NHSO_2R^5$, $NHCO_2R^6$, $NHCOR^6$, $NHCONR^4$, $NHSO_2NR^5R^6$, or heteroaryl, the latter which may be optionally substituted by halogen, CN or $OR^7$.

Suitably $R^1$ is one or more substituents independently selected from $NR^4SO_2R^5$, $NR^4CO_2R^6$, $NR^4COR^6$, $NR^4SO_2NR^5R^6$, $NHSO_2R^5$, $NHCO_2R^6$, $NHCOR^6$, $NHSO_2NR^5R^6$, or heteroaryl, the latter which may be optionally substituted by halogen, CN or $OR^7$.

Preferably $R^1$ is $NR^4COR6^4$, $NHSO_2R^4$, $NHCOR^6$ or a heteroaryl group.

More preferably $R^1$ is $NHSO_2Me$ or $NR^4COMe$, NHCON-Halkyl, $NR^4COcyclopropyl$, $NHSO_2heteroaryl$, $NHSO_2NMe_2$, $NHCONR^4$, a 5-6 membered heteroaromatic group containing 1-2 heteroatoms. Most preferably $R^1$ is $NHSO_2Me$ or $NR^4COMe$, NHCONHalkyl, dimethyoxazole, pyrimidine or pyrazine. Even more preferably $R^1$ is NHCOMe.

The R¹ groups can be present at any suitable position on the indole ring. Preferably the R¹ group(s) is (are) at the 5-position and/or 4-position.

Preferably $R^2$ is $C_{1-6}$alkyl or hydrogen, more preferably $C_{1-6}$alkyl or hydrogen, still more preferably methyl or hydrogen. Most preferably $R^2$ is methyl.

Preferably $R^3$ is quinolyl or phenyl, the latter is optionally substituted by halogen, alkoxy, $SO_2R^4$, more preferably the phenyl group is substituted by chloro, methoxy, methylsulfone or ethylsulfone.

Substituents can be present on any suitable position of an $R^3$ group. Preferably, if $R^3$ is phenyl the substituents is/are present at the 2, 3 and 4-positions. Most preferably a single substituent is present at the 4-position.

Preferred compounds of the invention include:
4-(acetylamino)-3-[(4-chlorophenyl)thio]-2-methyl-1H-indole-1-acetic acid;
3-[(4-chlorophenyl)thio]-2-methyl-4-[(methylsulfonyl)amino]-1H-indole-1-acetic acid;
3-[(4-chlorophenyl)thio]-2-methyl-4-(5-pyrimidinyl)-1H-indole-1-acetic acid;
3-[(4-chlorophenyl)thio]-2-methyl-4-pyrazinyl-1H-indole-1-acetic acid;
3-[(2-chlorophenyl)thio]-2-methyl-5-[(methylsulfonyl)amino]-1H-indole-1-acetic acid;
3-[(3-chlorophenyl)thio]-2-methyl-4-[(methylsulfonyl)amino]-1H-indole-1-acetic acid;
3-[(4-chlorophenyl)thio]-2-methyl-4-[(methylsulfonyl)amino]-1H-indole-1-acetic acid;
3-[(3-methoxyphenyl)thio]-2-methyl-4-[(methylsulfonyl)amino]-1H-indole-1-acetic acid;
3-[(4-methoxyphenyl)thio]-2-methyl-4-[(methylsulfonyl)amino]-1H-indole-1-acetic acid;
3-[(2-trifluoromethylphenyl)thio]-2-methyl-4-[(methylsulfonyl)amino]-1H-indole-1-acetic acid;
3-[(8-Quinolinyl)thio]-2-methyl-4-[(methylsulfonyl)amino]-1H-indole-1-acetic acid;
3-[(2-(methylethyl)phenyl)thio]-2-methyl-4-[(methylsulfonyl)amino]-1H-indole-1-acetic acid;
5-(acetylamino)-3-[(4-chlorophenyl)thio]-2-methyl-1H-indole-1-acetic acid;
4-(acetylethylamino)-3-[(4-chlorophenyl)thio]-2-methyl-1H-indole-1-acetic acid;
3-[(4-chlorophenyl)thio]-4-[cyclopropylcarbonyl)amino]-2-methyl-1H-indole-1-acetic acid;
4-(benzoylamino)-3-[(4-chlorophenyl)thio]-2-methyl-1H-indole-1-acetic acid;
4-(acetylamino)-3-[(3-chlorophenyl)thio]-2-methyl-1H-indole-1-acetic acid;
3-[(4-chlorophenyl)thio]-4-[[(dimethylamino)sulfonyl]amino]-2-methyl-1H-indole-1-acetic acid;
3-[(4-chlorophenyl)thio]-2-methyl-4-[[(1-methyl-1H-imidazol-4-yl)sulfonyl]amino]-1H-indole-1-acetic acid;
3-[(4-chlorophenyl)thio]-2-methyl-4-[[(dimethylamino)acetyl]amino]-2-methyl-1H-indole-1-acetic acid;
4-(acetylamino)-2-methyl-3-[[4-(methylsulfonyl)phenyl]thio]-1H-indole-1-acetic acid;
4-(acetylamino)-3-[(2-chlorophenyl)thio]-2-methyl-1H-indole-1-acetic acid;
4-(acetylamino)-2-methyl-3-[[4-(ethylsulfonyl)phenyl]thio]-1H-indole-1-acetic acid;
3-[(4-chlorophenyl)thio]-4-[[(ethylamino)carbonyl]amino]-2-methyl-1H-indole-1-acetic acid;
3-[[4-(methylsulfonyl)phenyl]thio]-4-(5-pyrimidinyl)-1H-indole-1-acetic acid
2-methyl-3-[[4-(methylsulfonyl)phenyl]thio]-4-(2-thiophenyl)-1H-indole-1-acetic acid
4-(3,5-dimethyl-4-isoxazolyl)-2-methyl-3-[[4-(methylsulfonyl)phenyl]thio]-1H-indole-1-acetic acid
4-(3-furanyl)-2-methyl-3-[[4-(methylsulfonyl)phenyl]thio]-1H-indole-1-acetic acid
2-methyl-4-[(methylsulfonyl)amino]-3-[[4-(methylsulfonyl)phenyl]thio]-1H-indole-1-acetic acid
2-methyl-5-[(methylsulfonyl)amino]-3-[[3-(methylsulfonyl)phenyl]thio]-1H-indole-1-acetic acid
2-methyl-5-[(methylsulfonyl)amino]-3-[[2-(methylsulfonyl)phenyl]thio]-1H-indole-1-acetic acid
2-methyl-3-[[4-(methylsulfonyl)phenyl]thio]-5-(5-pyrimidinyl)-1H-indole-1-acetic acid
2-methyl-3-[[4-(methylsulfonyl)phenyl]thio]-5-(3-thiophenyl)-1H-indole-1-acetic acid
5-(3,5-dimethyl-4-isoxazolyl)-2-methyl-3-[[4-(methylsulfonyl)phenyl]thio]-1H-indole-1-acetic acid
2-methyl-3-[[4-(methylsulfonyl)phenyl]thio]-5-(3-pyridinyl)-1H-indole-1-acetic acid
2-methyl-3-[[4-(methylsulfonyl)phenyl]thio]-5-(1H-pyrazolyl)-1H-indole-1-acetic acid
4-(acetylamino)-3-[(4-cyanophenyl)thio]-2-methyl-1H-indole-1-acetic acid and pharmaceutically acceptable salts and solvates thereof.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

The compound of formula (I) above may be converted to a pharmaceutically acceptable salt or solvate thereof, preferably a basic addition salt such as ammonium, sodium, potassium, calcium, aluminium, lithium, magnesium, zinc, benzathine, chloroprocaine, choline, diethanolamine, ethanolamine, ethyldiamine, meglumine, tromethamine or procaine, or an acid addition salt such as a hydrochloride, hydrobromide, phosphate, acetate, fumarate, maleate, tartrate, citrate, oxalate, methanesulphonate or p-toluenesulphonate. Preferred salts include sodium and ammonium salts.

It will be appreciated by those skilled in the art that in the processes of the present invention certain functional groups in the starting reagents or intermediate compound may need to be protected by protecting groups. Thus, the preparation of the compound of formula (I) may involve, at an appropriate stage, the removal of one or more protecting groups. The protection and deprotection of functional groups is fully described in 'Protective Groups in Organic Chemistry', edited by J. W. P. McOmie, Plenum Press (1973), and 'Protective Groups in Organic Synthesis', 3rd edition, T. W. Greene & P. G. M. Wuts, Wiley-Interscience (1999).

In a further aspect the invention provides a process for the preparation of a compound of formula (I) or a pharmaceutically acceptable salt or solvate thereof which comprises reaction of a compound of formula (II):

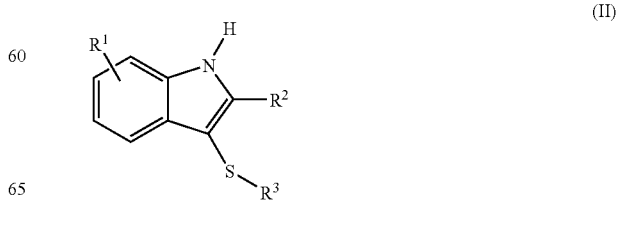

in which $R^1$, $R^2$ and $R^3$ are as defined in formula (I) or are protected derivatives thereof, with a compound of formula (IIA):

$$L\text{-}CH_2CO_2R^{17} \tag{IIA}$$

where $R^{17}$ is an alkyl group and L is a leaving group such as a halogen atom, in the presence of a base, and optionally thereafter in any order removing any protecting group hydrolysing the ester group $R^{17}$ to the corresponding acid forming a pharmaceutically acceptable salt or solvate.

The reaction can be carried out in a suitable solvent such as THF using a base such as sodium hydride or the like. Suitable groups $R^{17}$ include $C_{1-6}$ alkyl groups such as methyl, ethyl or tertiary-butyl. Suitable L is a leaving group such as halo, in particular bromo Preferably the compound of formula (IIA) is ethyl, methyl or tertiary-butyl bromoacetate.

Hydrolysis of the ester group $R^{17}$ can be carried out using routine procedures, for example by stirring with aqueous sodium hydroxide or trifluoroacetic acid.

It will be appreciated that certain functional groups may need to be protected using standard protecting groups. The protection and deprotection of functional groups is for example, described in 'Protective Groups in Organic Chemistry', edited by J. W. F. McOmie, Plenum Press (1973), and 'Protective Groups in Organic Synthesis', 3rd edition, T. W. Greene & P. G. M. Wuts, Wiley-Interscience (1999).

Compounds of formula (II), in which $R^1$ is $NRSO_2R$ or $NRC(O)R$ can be from compounds of formula (III), by reaction with an acylating reagent such as acetyl chloride or sulfonyl chloride.

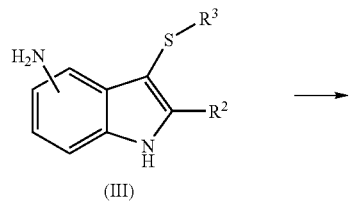

(III)

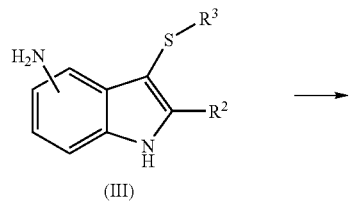

(II)

Compounds of formula (II) can be prepared from compounds of formula (IV) by reduction using a hydrogen and a suitable catalyst, preferably, the catalyst used is palladium or platinum on activated carbon in the presence of a polar solvent such as ethanol.

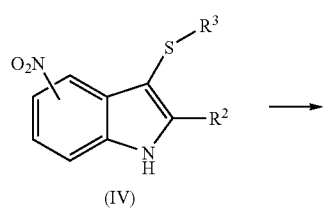

(IV)

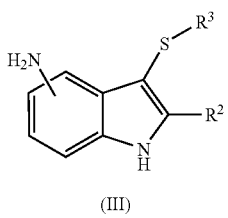

(III)

Compounds of formula (IV) can be prepared from compounds of formula (V) and (VI)

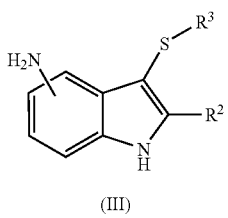

(V)      (VI)

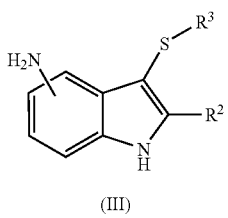

(IV)

in which $R^1$, $R^2$ and $R^3$ are as defined in formula (I).

Preferably the reaction is carried out in a suitable solvent, such as dichloromethane or THF, using a chlorinating agent such as sulfonyl chloride or tert-butyl hypochlorite.[1]

Compounds of formulae (V) and (VI) are commercially available or can be prepared using standard chemistry well known in the art.

Certain compounds of formula (I) can be prepared from compounds of formula (VII) where X=halogen, preferably bromine or iodine, by reaction with organostannanes (Stille couplings) or boronic acids (Suzuki couplings) using palladium catalysis. Preferably the catalysts used are tetrakis palladium triphenylphosphine(0), or palladium(II)acetate in the presence of a phosphine ligand such as tri-ortho tolyl phosphine, in a suitable solvent such as toluene or methanol at 80° C. The group $R^{17}$ is subsequently hydrolysed as outlined previously.

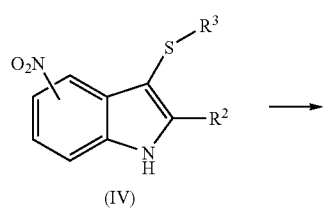

(VII)

-continued

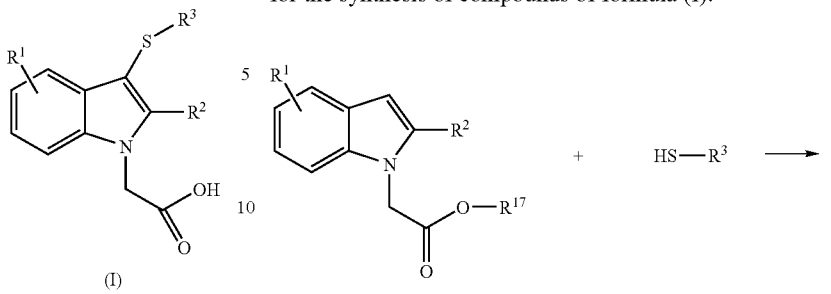

(I)

Compounds of formula (VII) are prepared from compounds of formula (II) with compounds of formula (IIA) as outlined previously:

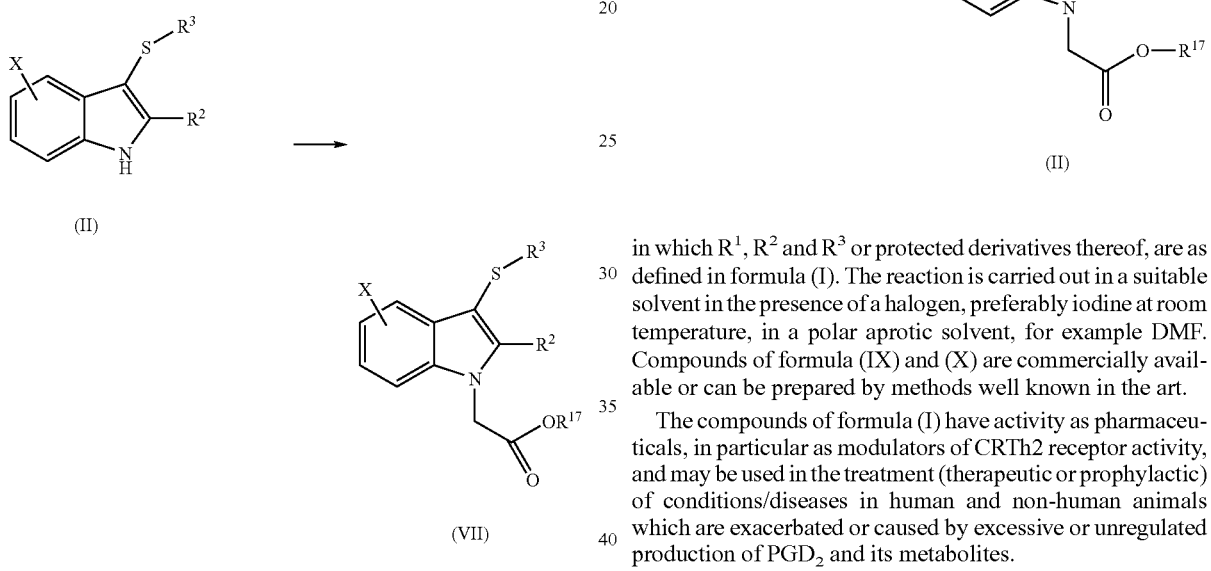

(II)

(VII)

Compounds of formula (II), where X is halogen are prepared by reacting a compound of formula (VIII) with a compound of formula (VI):

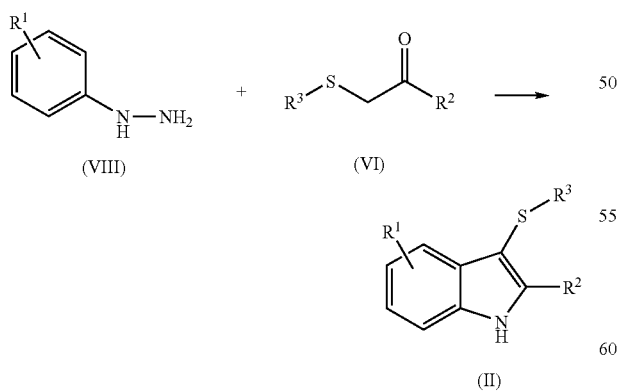

(VIII)     (VI)

(II)

in which $R^1$, $R^2$ and $R^3$ are as defined in formula (I).

Compounds of formula (II) can be prepared by reacting a compound of formula (IX) with a compound of formula (X), with subsequent hydrolysis of the ester as outlined previously for the synthesis of compounds of formula (I):

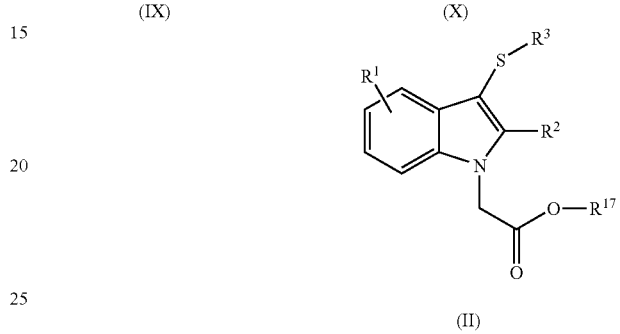

(IX)     (X)

(II)

in which $R^1$, $R^2$ and $R^3$ or protected derivatives thereof, are as defined in formula (I). The reaction is carried out in a suitable solvent in the presence of a halogen, preferably iodine at room temperature, in a polar aprotic solvent, for example DMF. Compounds of formula (IX) and (X) are commercially available or can be prepared by methods well known in the art.

The compounds of formula (I) have activity as pharmaceuticals, in particular as modulators of CRTh2 receptor activity, and may be used in the treatment (therapeutic or prophylactic) of conditions/diseases in human and non-human animals which are exacerbated or caused by excessive or unregulated production of $PGD_2$ and its metabolites.

A compound of the invention, or a pharmaceutically acceptable salt thereof, can be used in the treatment of:

(1) (respiratory tract)—obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus.

(2) (bone and joints) arthritides associated with or including osteoarthritis/osteoarthrosis, both primary and secondary to e.g. congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthropathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymyalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthralgias, tendonititides, and myopathies.

(3) (skin) psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions.

(4) (eyes) blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial.

(5) (gastrointestinal tract) glossitis, gingivitis, periodontitis; oesophagitis, including reflux; eosinophilic gastroenteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema).

(6) (abdominal) hepatitis, including autoimmune, alcoholic and viral; fibrosis and cirrhosis of the liver; cholecystitis; pancreatitis, both acute and chronic.

(7) (genitourinary) nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female).

(8) (Allograft rejection) acute and chronic following, for example, transplantation of kidney, heart, liver, lung, bone marrow, skin or cornea or following blood transfusion; or chronic graft versus host disease;

(9) (CNS) Alzheimer's disease and other demyelinating disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes.

(10) Other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome.

(11) Other disorders with an inflammatory or immunological component; including acquired immune deficiency syndrome (AIDS), leprosy, Sezary syndrome, and paraneoplastic syndromes.

(12) (Cardiovascular); atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (e.g. syphilitic); vasculitides; disorders of the proximal and peripheral veins including phlebitis and thrombosis, including deep vein thrombosis and complications of varicose veins.

(13) (Oncology) treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes.

(14) Diseases associated with raised levels of $PGD_2$ or its metabolites.

Thus, the present invention provides a compound of formula (I), or a pharmaceutically-acceptable salt or solvate thereof, as hereinbefore defined for use in therapy.

Preferably the compounds of the invention are used to treat diseases in which the chemokine receptor belongs to the CRTh2 receptor subfamily.

Particular conditions which can be treated with the compounds of the invention are asthma, rhinitis and other diseases in which raised levels of $PGD_2$ or its metabolites. It is preferred that the compounds of the invention are used to treat asthma.

In a further aspect, the present invention provides the use of a compound of formula (I), or a pharmaceutically acceptable salt or solvate thereof, as hereinbefore defined in the manufacture of a medicament for use in therapy in particular for the treatment of a disease mediated by CRTh2 such as asthma or rhinitis.

Thus, the present invention provides a compound of formula (I), or a pharmaceutically-acceptable salt or solvate thereof, as hereinbefore defined for use in therapy.

Preferably the compounds of the invention are used to treat diseases in which the chemokine receptor belongs to the CRTh2 receptor subfamily.

Particular conditions which can be treated with the compounds of the invention are asthma, rhinitis and other diseases in which raised levels of $PGD_2$ or its metabolites. It is preferred that the compounds of the invention are used to treat asthma.

The invention further relates to combination therapies wherein a compound of formula (1) or a pharmaceutically acceptable salts, solvate or in vivo hydrolysable ester thereof, or a pharmaceutical composition or formulation comprising a compound of formula (1) is administered concurrently or sequentially with therapy and/or an agent for the treatment of any one of asthma, allergic rhinitis, cancer, COPD, rheumatoid arthritis, psoriasis, inflammatory bowel diseases, osteoarthritis or osteoporosis.

In particular, for the treatment of the inflammatory diseases rheumatoid arthritis, psoriasis, inflammatory bowel disease, COPD, asthma and allergic rhinitis the compounds of the invention may be combined with agents such as TNF-α inhibitors such as anti-TNF monoclonal antibodies (such as Remicade, CDP-870 and $D_2E_7$.) and TNF receptor immunoglobulin molecules (such as Enbrel.reg.), non-selective COX-1/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin), COX-2 inhibitors (such as meloxicam, celecoxib, rofecoxib, valdecoxib and etoricoxib) low dose methotrexate, lefunomide; ciclesonide; hydroxychloroquine, d-penicillamine, auranofin or parenteral or oral gold.

The present invention still further relates to the combination of a compound of the invention together with a leukotriene biosynthesis inhibitor, 5-lipoxygenase (5-LO) inhibitor or 5-lipoxygenase activating protein (FLAP) antagonist such as zileuton; ABT-761; fenleuton; tepoxalin; Abbott-79175; Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746,530; indole and quinoline compounds such as MK-591, MK-886, and BAY x 1005.

The present invention still further relates to the combination of a compound of the invention together with a receptor antagonist for leukotrienes $LTB_4$., $LTC_4$., $LTD_4$., and $LTE_4$. selected from the group consisting of the phenothiazin-3-ones such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention together with a PDE4 inhibitor including inhibitors of the isoform PDE4D.

The present invention still further relates to the combination of a compound of the invention together with a antihistaminic $H_1$. receptor antagonists such as cetirizine, loratadine, desloratadine, fexofenadine, astemizole, azelastine, and chlorpheniramine.

The present invention still further relates to the combination of a compound of the invention together with a gastroprotective $H_2$. receptor antagonist.

The present invention still further relates to the combination of a compound of the invention together with an $\alpha_1$- and $\alpha_2$-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride.

The present invention still further relates to the combination of a compound of the invention together with anticholinergic agents such as ipratropium bromide; tiotropium bromide; oxitropium bromide; pirenzepine; and telenzepine.

The present invention still further relates to the combination of a compound of the invention together with a $\beta_1$- to $\beta_4$-adrenoceptor agonists such as metaproterenol, isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

The present invention still further relates to the combination of a compound of the invention together with an insulin-like growth factor type I (IGF-1) mimetic.

The present invention still further relates to the combination of a compound of the invention together with an inhaled glucocorticoid with reduced systemic side effects, such as prednisone, prednisolone, flunisolide, triamcinolone acetonide, beclomethasone dipropionate, budesonide, fluticasone propionate, and mometasone furoate.

The present invention still further relates to the combination of a compound of the invention together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MB-10), and stromelysin-3 (MMP-11) and MMP-12.

The present invention still further relates to the combination of a compound of the invention together with other modulators of chemokine receptor function such as CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention still further relates to the combination of a compound of the invention together with antiviral agents such as Viracept, AZT, acyclovir and famciclovir, and antisepsis compounds such as Valant.

The present invention still further relates to the combination of a compound of the invention together with cardiovascular agents such as calcium channel blockers, lipid lowering agents such as statins, fibrates, beta-blockers, Ace inhibitors, Angiotensin-2 receptor antagonists and platelet aggregation inhibitors.

The present invention still further relates to the combination of a compound of the invention together with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metrifonate.

The present invention still further relates to the combination of a compound of the invention together with (i) tryptase inhibitors; (ii) platelet activating factor (PAF) antagonists; (iii) interleukin converting enzyme (ICE) inhibitors; (iv) IMPDH inhibitors; (v) adhesion molecule inhibitors including VLA-4 antagonists; (vi) cathepsins; (vii) MAP kinase inhibitors; (viii) glucose-6 phosphate dehydrogenase inhibitors; (ix) kinin-B$_1$. and B$_2$.-receptor antagonists; (x) anti-gout agents, e.g., colchicine; (xi) xanthine oxidase inhibitors, e.g., allopurinol; (xii) uricosuric agents, e.g., probenecid, sulfinpyrazone, and benzbromarone; (xiii) growth hormone secretagogues; (xiv) transforming growth factor (TGFβ); (xv) platelet-derived growth factor (PDGF); (xvi) fibroblast growth factor, e.g., basic fibroblast growth factor (bFGF); (xvii) granulocyte macrophage colony stimulating factor (GM-CSF); (xviii) capsaicin cream; (xix) Tachykinin NK$_1$ and NK$_3$ receptor antagonists selected from the group consisting of NKP-608C; SB-233412 (talnetant); and D-4418; (xx) elastase inhibitors selected from the group consisting of UT-77 and ZD0892; (xxi) TNFα converting enzyme inhibitors (TACE); (xxii) induced nitric oxide synthase inhibitors (iNOS) or (xxiii) chemoattractant receptor-homologous molecule expressed on TH2 cells.

The compounds of the present invention may also be used in combination with osteoporosis agents such as roloxifene, droloxifene, lasofoxifene or fosomax and immunosuppressant agents such as FK-506, rapamycin, cyclosporine, azathioprine, and methotrexate.

The compounds of the invention may also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intrarticular therapies such as corticosteroids and hyaluronic acids such as hyalgan and synvisc and P2X7 receptor antagonists.

The compounds of the invention can also be used in combination with existing therapeutic agents for the treatment of cancer. Suitable agents to be used in combination include:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea, gemcitabine and paclitaxel (Taxol®); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3- chlorofluorophenyl)-7-methoxy-6-(3-morpholinopropoxy) quinazolinamine (gefitinib, AZD1839), N-(3- ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy) quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO99/02166, WO00/40529, WO00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-dug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of CRTh2 receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating diseases mediated by PGD2 or its metabolites wherein the prostanoid binds to its receptor (especially CRTh2) receptor, which comprises administering to a patient a therapeutically effective amount of a compound of formula (I), or a pharmaceutically acceptable salt, solvate or prodrug thereof, as hereinbefore defined.

The invention also provides a method of treating an inflammatory disease, especially psoriasis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

For the above-mentioned therapeutic uses the dosage administered will, of course, vary with the compound employed, the mode of administration, the treatment desired and the disorder indicated.

The compound of formula (I), prodrugs and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as herein before defined, in association with a pharmaceutically acceptable adjuvant, diluent or carrier.

The present invention also provides a pharmaceutical composition comprising a compound of formula (I), or a pharmaceutically acceptable salt or solvate thereof, as herein before defined, in association with a pharmaceutically acceptable adjuvant, diluent or carrier.

The invention will now be illustrated by the following non-limiting examples in which, unless stated otherwise:

(i) the title and sub-titled compounds of the examples and methods were named using the ACD labs/name program (version 6.0) from Advanced Chemical Development Inc, Canada;

(ii) unless stated otherwise, reverse phase preparative HPLC was conducted using a Symmetry, NovaPak or Ex-Terra reverse phase silica column;

(iii) Flash column chromatography refers to normal phase silica chromatography (iv) solvents were dried with $MgSO_4$ or $Na_2SO_4$ (v) Evaporations were carried out by rotary evaporation in vacuo and work-up procedures were carried out after removal of residual solids such as drying agents by filtration;

(vi) Unless otherwise stated, operations were carried out at ambient temperature, that is in the range 18-25° C. and under an atmosphere of an inert gas such as argon or nitrogen;

(vii) yields are given for illustration only and are not necessarily the maximum attainable;

(viii) the structures of the end-products of the formula (1) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(ix) intermediates were not generally fully characterised and purity was assessed by thin layer chromatography (TLC), high-performance liquid chromatography (HPLC), mass spectrometry (MS), infra-red (IR) or NMR analysis;

(x) mass spectra (MS): generally only ions which indicate the parent mass are reported when given, $^1$H NMR data is quoted in the form of delta values for major diagnostic protons, given in parts per million (ppm) relative to tetramethylsilane (TMS) as an internal standard;

(xi) the following abbreviations are used:
M.p.=melting point
THF=tetrahydrofuran
EtOAc=ethyl acetate
MCPBA=meta chloroperbenzoic acid
DMF=N,N-dimethyl formamide
$MgSO_4$=magnesium sulfate
$Na_2SO_4$=sodium sulfate
$NaHCO_3$=sodium hydrogen carbonate

EXAMPLE 1

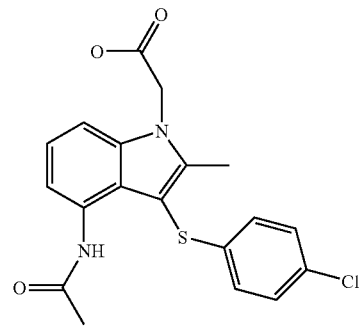

4-(Acetylamino)-3-[(4-chlorophenyl)thio]-2-methyl-1H-indole-1-acetic acid i) 3-[(4-chlorophenyl)thio]-2-methyl-4-nitro-1H-indole To a stirred solution of 3-nitroaniline (8 g) in THF (700 ml) cooled to −78° C. was added tert-butyl hypochlorite (6.3 g) dropwise over 5 minutes. The reaction was allowed to warm to −65° C. over 20 minutes before 1-[4-chlorophenyl)thio]-2-propanone (11.6 g) was added as a solution in THF (20 ml). After 2 hours triethylamine (8.1 ml) was added and the reaction allowed to warm to room temperature. 2M HCl (aq) was added to the reaction mixture before concentration in vacuo. The residue was slurried in methanol and the solid which precipitated isolated by filtration to give the sub-title compound (5.8 g).

$^1$H NMR (DMSO-d6) δ 12.55 (s, 1H), 7.76 (dd, 1H), 7.63 (dd, 1H), 7.31-7.22 (m, 3H), 6.91 (dd, 2H), 2.47 (s, 3H)

ii) 3-[(4-chlorophenyl)thio]-2-methyl-4-nitro-1H-indole-acetic acid, ethyl ester To a stirred suspension of sodium hydride, 60% dispersion in mineral oil, (0.85 g) in THF (100 ml) was added the product from part (i) (5.6 g) as a solution in THF (50 ml). After stirring at room temperature for 30 minutes ethyl bromoacetate (2.3 ml) was added dropwise over 10 minutes. After 2 hours the reaction was concentrated in vacuo, the residue dissolved in ethyl acetate, washed with water, brine, dried (MgSO$_4$) and concentrated in vacuo. Recrystallisation from ethanol gave the sub-title compound (5 g).

$^1$H NMR (DMSO-d6) δ 7.97 (dd, 1H), 7.65 (dd, 1H), 7.35 (t, 1H), 7.26 (dt, 2H), 6.92 (dt, 2H), 5.40 (s, 2H), 4.19 (q, 2H), 2.45 (s, 3H), 1.22 (t, 3H).

iii) 4-amino-3-[(4-chlorophenyl)thio]-2-methyl-1H-indole-acetic acid, ethyl ester A suspension of the product from part (ii) (2.25 g) in ethanol (170 ml) was stirred in the presence of 5% Pt/C (0.5 g) under 2 bar pressure of H$_2$. After stirring overnight the catalyst was removed by filtration and the filtrates concentrated in vacuo. Purification by flash column chromatography (14% EtOAc/hexane as eluent) to give the sub-title compound (1.4 g).

$^1$H NMR (DMSO-d6) δ 7.30 (dd, 2H), 7.00 (dt, 2H), 6.85 (t, 1H), 6.68 (dd, 1H), 6.23 (dd, 1H), 5.33 (s, 2H), 5.09 (s, 2H), 4.16 (q, 2H), 2.33 (s, 3H), 1.21 (t, 3H).

3-[(4-chlorophenyl)thio]-4-(ethylamino)-2-methyl-1H-indole-1-acetic acid, ethyl ester was also isolated as a by product from the reaction (0.33 g).

$^1$H NMR (DMSO-d6) δ 7.32 (dd, 2H), 7.01 (dd, 2H), 6.95 (t, 1H), 6.73 (d, 1H), 6.16 (d, 1H), 5.70 (t, 1H), 5.11 (s, 2H), 4.16 (q, 2H), 3.05 (dt, 2H), 2.34 (s, 3H), 1.21 (t, 3H), 1.02 (t, 3H).

iv) 4-(acetylamino)-3-[(4-chlorophenyl)thio]-2-methyl-1H-indole-acetic acid, ethyl ester To a solution of the product from part (iii) (0.5 g) in dichloromethane (10 ml) was added triethylamine (0.18 ml) and acetyl chloride (0.1 ml), the reaction was stirred at room temperature for 30 minutes. The mixture was then adsorbed onto silica gel and purified by column chromatography (33% EtOAc/hexane as eluent) to give the sub-title compound (0.52 g).

$^1$H NMR (DMSO-d6) δ 9.51 (s, 1H), 7.46 (d, 1H), 7.34-7.27 (m, 3H), 7.11 (t, 1H), 6.97 (d, 2H), 5.24 (s, 2H), 4.18 (q, 2H), 2.39 (s, 3H), 1.86 (s, 3H), 1.21 (t, 3H).

v) 4-(acetylamino)-3-[(4-chlorophenyl)thio]-2-methyl-1H-indole-acetic acid

To a solution of the product from part (iv) (0.31 g) in THF (10 ml) was added a 1M solution of NaOH (aq) (0.75 ml). The reaction was stirred overnight at room temperature. The reaction mixture was concentrated in vacuo and the residue dissolved/suspended in water. The pH was adjusted to 2 using dilute HCl (aq) and the solid which precipitated isolated by filtration. Recrystallisation from acetonitrile gave the title compound (0.16 g).

$^1$H NMR (DMSO-d6) δ 13.21 (s, 1H), 9.51 (s, 1H), 7.46 (d, 1H), 7.33-7.27 (m, 3H), 7.11 (t, 1H), 6.98 (d, 2H), 5.12 (s, 2H), 2.39 (s, 3H), 1.85 (s, 3H). APCI+ [M+H] 389 M.p. dec>266° C.

EXAMPLE 2

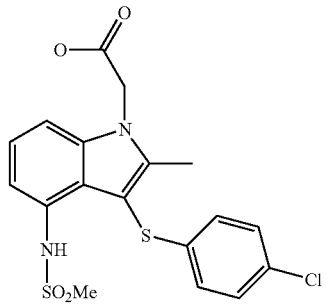

3-[(4-Chlorophenyl)thio]-2-methyl-4-[(methylsulfonyl)amino]1H-indole-1-acetic acid i) 3-[(4-chlorophenyl)thio]-2-methyl-4-[(methylsulfonyl)amino]-1H-indole-1-acetic acid, ethyl ester To a solution of the product from Example 1 part (iii) (0.5 g) in dichloromethane (10 ml) were added triethylamine (0.18 ml) and methane sulfonyl chloride (0.1 ml), and the reaction was stirred at room temperature for 2 hours before heating at reflux overnight. The dichloromethane was removed in vacuo, acetonitrile added (10 ml) and the reaction was heated to 60° C. for 5 hours. The mixture was adsorbed onto silica gel and purified by column chromatography (33% EtOAc/hexane as eluent) to give the sub-title compound (0.44 g).

$^1$H NMR (DMSO-d6) δ 8.80 (s, 1H), 7.39 (d, 1H), 7.32 (d, 2H), 7.20-7.07 (m, 2H), 6.97 (d, 2H), 5.27 (s, 21, 4.18 (q, 2H), 2.74 (s, 3H), 2.38 (s, 3H), 1.22 (t, 3H).

ii) 3-[(4-chlorophenyl)thio]-2-methyl-4-[(methylsulfonyl)amino]-1H-indole-1-acetic acid The title compound was prepared by the method of Example 1 part (v), using the product from part (i).

$^1$H NMR (DMSO-d6) δ 13.25 (s, 1H), 8.80 (s, 1H), 7.39 (d, 1H), 7.32 (m, 2H), 7.16 (t, 1H), 7.09 (d, 1H), 6.98 (dt, 2H), 5.15 (s, 2H), 2.73 (s, 3H), 2.38 (s, 3H). APCI− [M−H] 423 M.p. dec>243° C.

EXAMPLE 3

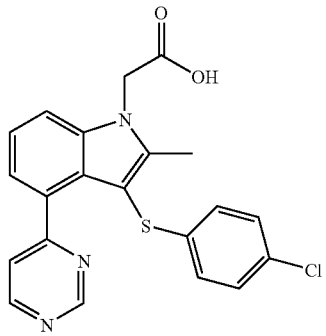

3-[(4-Chlorophenyl)thio]-2-methyl-4-(5-pyrimidinyl)-1H-indole-1-acetic acid i) 4-bromo-3-[4(-chlorophenyl)thio]-2-methyl-1H-indole 3-bromophenyl hydrazine hydrochloride (15.34 g) in water (80 ml) was added to a suspension of 1-[(4-chlorophenyl)

thio]acetone (13.77 g) in acetonitrile (200 ml) and stirred overnight at room temperature and then concentrated in vacuo. The residue was partitioned between aqueous sodium hydrogen carbonate and dichloromethane. The organic phase was washed with brine, dried (MgSO$_4$) and concentrated in vacuo. The residual oil was treated with acetic acid (70 ml) and heated at 80° C. overnight. The reaction mixture was poured into water, basified with aqueous sodium hydroxide and extracted with EtOAc (twice). The combined organics were washed (brine), dried (MgSO$_4$) and concentrated in vacuo.

The mixture was purified by flash column chromatography (40% EtOAc/hexane as eluent) to give the sub-title compound (4.43 g).

$^1$H NMR (DMSO-d6) δ 7.31 (s, 1H), 7.30 (d, 2H), 7.13 (dt, 2H), 7.02 (t, 1H), 6.94 (dt, 2H), 2.52 (s, 3H).

ii) 4-bromo-3-[(4-chlorophenyl)thio]-2-methyl-1H-indole-1-acetic acid, 1,1-dimethylethyl ester The sub-title compound was prepared by the method of Example 1 part (ii) using the product of part (i) and t-butyl bromoacetate. The product was purified using column chromatography (10% EtOAc/hexane as eluent).

$^1$H NMR (CDCl$_3$: δ 7.31 (dd, 1H), 7.21 (dd, 1H), 7.14-7.10 (m, 2H), 7.05 (t, 1H), 6.94-6.91 (m, 2H), 4.77 (s, 2H), 2.49 (s, 3H), 1.43 (s, 9H).

iii) 3-[(4-chlorophenyl)thio]-2-methyl-4-(5-pyrimidinyl)-1H-indole-1-acetic acid, 1,1-dimethylethyl ester To a solution/suspension of the product of part (ii) (500 mg) in toluene (4 ml) was added ethanol (1 ml), 5-pyrimidinyl-boronic acid (133 mg), 2M sodium carbonate (1.5 ml) and finally tetrakis(triphenylphosphine)paladium (0), (125 mg). The mixture was heated at 100° C. for 3 days. Purification by column chromatography (eluent 2:1 Hexane:EtOAc) gave the sub-title compound as an orange solid (140 mg).

$^1$H NMR (DMSO-d6) δ 8.99 (s, 1H), 8.57 (s, 2H), 7.68 (d, 1H), 7.10 (dd, 2H), 6.99 (d, 1H), 7.30 (dt, 1H), 6.46 (dd, 2H), 5.21 (s, 2H), 2.42 (s, 3H), 1.45 (s, 9H).

iii) 3-[(4-chlorophenyl)thio]-2-methyl-4-(5-pyrimidinyl-1H-indole-1-acetic acid

The title compound was prepared by the method of Example 1 part (v) using the product from step (iii), with purification by reverse phase hplc (MeCN/NH$_3$(aq) as eluent).

$^1$H NMR (DMSO-d6) δ 8.99 (s, 1H), 8.57 (s, 2H), 7.69 (d, 1H), 7.29 (t, 1H), 7.10 (m, 2H), 6.98 (d, 1H), 6.47 (m, 2H), 5.19 (s, 2H), 2.43 (s, 3H). APCI− [M−H] 408

EXAMPLE 4

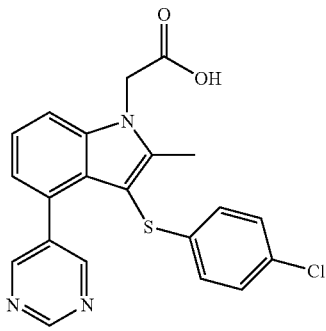

3-[(4-Chlorophenyl)thio]-2-methyl-4-pyrazinyl-1H-indole-1-acetic acid i) 3-[(4-chlorophenyl)thio]-2-methyl-4-pyrazinyl-1H-indole-1-acetic acid, 1,1-dimethylethyl ester To a solution of the product from Example 3 part (ii) (0.4 g) in toluene (4 ml) was added 2-tributylstannylpyrazine (0.32 g) and tetrakis(triphenylphosphine)palladium (0) (0.1 g). The reaction mixture was heated to 80° C. for 18 hours. The mixture was adsorbed onto silica and purified using column chromatography (33% EtOAc/hexane as eluent) to give the sub-title compound (160 mg).

$^1$H NMR (DMSO-d6) δ 8.52 (d, 1H), 8.47 (d, 1H), 8.41 (t, 1H), 7.68 (d, 1H), 7.30 (t, 1H), 7.13-7.09 (m, 3H), 6.55 (m, 2H), 5.21 (s, 2H), 2.40 (s, 3H), 1.44 (s, 9H).

ii) 3-[(4-chlorophenyl)thio]-2-methyl-4-pyrazinyl-1H-indole-1-acetic acid

The title compound was prepared by the method of Example 1 part (v), with purification by preparative hplc (MeCN/NH$_3$ (aq) as eluent).

$^1$H NMR (DMSO-d6) δ 8.50 (d, 1H), 8.45 (d, 1H), 8.41 (dd, 1H), 7.56 (dd, 1H), 7.22 (dd, 1H), 7.13-7.09 (m, 2H), 7.04 (dd, 1H), 6.58 (dt, 2H), 4.68 (s, 2H), 2.38 (s, 3H) APCI− [M−H] 408

EXAMPLE 5

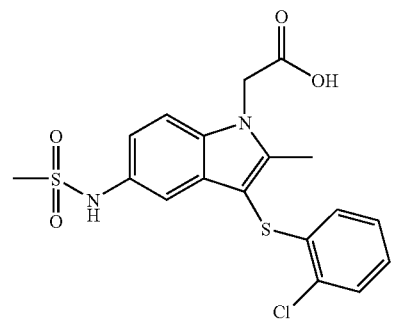

3-[(2-Chlorophenyl)thio]-2-methyl-5-[(methylsulfonyl)amino]-1H-indole-1-acetic acid i) 2-methyl-5-nitro-1H-indole-1-acetic acid ethyl ester 2-Methyl-5-nitro-1H-indole (5.3 g) was dissolved in dimethyl formamide (20 ml) and to it added sodium hydride (1.2 g) for the mixture to be stirred for 1 hour. Ethyl bromoacetate (6.8 g) was added all at once and a precipitate started to form. The mixture was quenched with 1% aqueous acetic acid and the precipitate collected by filtration and washed thoroughly with water, triturated with diethyl ether and dried under vacuum to give pure sub-title product (6.2 g).

$^1$H NMR (DMSO-d6) δ 8.45 (d, 1H), 7.96 (dd, 1H), 7.59 (d, 1H), 6.56 (s, 1H), 5.21 (s, 2H), 4.16 (q, 2H), 2.37 (s, 3H), 1.19 (t, 3H). APCI− [M−H] 263 ii) 5-amino-2-methyl-1H-indole-1-acetic acid, ethyl ester

A suspension of 2-methyl-5-nitro-1H-indole-1-acetic acid, ethyl ester (6.2 g) in ethanol (600 ml) in the presence of 10% palladium on charcoal (0.6 g) was stirred under a hydrogen atmosphere at 3 bar for 4 hours. The mixture was filtered through celite and the filtrate evaporated to give the sub-title compound as a pink viscous oil (5.3 g).
APCI– [M–H] 233 iii) 2-methyl-5-[(methylsulfonyl)amino]-1H-indole-1-acetic acids ethyl ester

Methanesulfonyl chloride (1.15 g) was added to a solution of 5-amino-2-methyl-1H-indole-1-acetic acid, ethyl ester (2.3 g) in triethylamine (1.7 ml) and dichloromethane (20 ml) at 0° C. a pink viscous oil for a pink viscous oil for and stirred at 20° C. for 1 hour. Water was added and the mixture extracted with dichloromethane, dried (Na$_2$SO$_4$) and evaporated to give the crude solid. This was purified by chromatography using silica (40:1 dichloromethane/ethyl acetate as eluent) to give the sub-title compound as a pink solid (1.4 g).
$^1$H NMR (DMSO-d6) δ 9.23 (s, 1H), 7.30 (m, 2H), 6.94 (dd, 1H), 6.23 (s, 1H), 5.03 (s, 2H), 4.14 (q, 2H), 2.85 (s, 3H), 2.31 (s, 3H), 1.19 (t, 3H). APCI– [M–H] 311 iv) 3-[(2-chlorophenyl)thio]2-methyl-5-[(methylsulfonyl)amino]-1H-indole-1-acetic acid, ethyl ester 2-methyl-5-[(methylsulfonyl)amino]-1H-indole-1-acetic acid, ethyl ester (0.31 g) and 2-chlorobenzenethiol (0.27 g) were dissolved in dimethyl formamide (3 ml) followed by addition of iodine 0.30 g) for the whole to be stirred at room temperature overnight. The mixture was poured into aqueous sodium thiosulphate (50 ml) and the resultant white precipitate collected by filtration and rinsed with water, dried under vacuum to be recrystallised from ethanol. The crystals were harvested and rinsed with isohexane and dried under vacuum to give the sub-title compound (0.20 g)
$^1$H NMR (DMSO-d6) δ 9.34 (s, 1H), 7.55 (d, 1H), 7.45 (m, H), 7.21 (d, 1H), 7.23-7.06 (m, 3H), 6.44 (m, 1H), 5.26 (s, 2H), 4.18 (q, 2H), 2.83 (s, 3H), 2.38 (s, 3H), 1.22 (t, 3H). APCI– [M–H] 453/455 v) 3-[(2-chlorophenyl)thio]-2-methyl-4-[methylsulfonyl)amino]-1H-indole-1-acetic acid The title compound was prepared by the method of Example 1 part (v) except that recrystallisation was not required. (0.10 g)
$^1$H NMR (DMSO-d6) δ 13.25 (s, 1H), 9.33 (s, 1H), 7.54 (d, 1H), 7.45 (dd, 1H), 7.21 (d, 1H), 7.08 (m, 3H), 6.45 (d, 1H), 5.13 (s, 2H), 2.83 (s, 3H), 2.38 (s, 3H). APCI– [M–H] 425/427 M.p. 212° C.

EXAMPLE 6

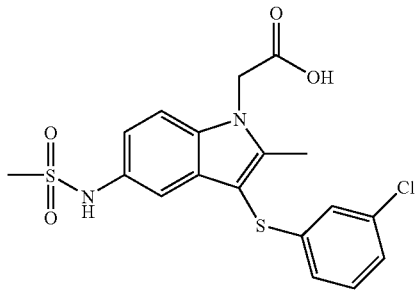

3-[(3-Chlorophenyl)thio]-2-methyl-5-[(methylsulfonyl)amino]-1H-indole-1-acetic acid i) 3-[(3-chlorophenyl)thio]-2-methyl-5-[(methylsulfonyl)amino]-1H-indole-1-acetic acid, ethyl ester The sub-title compound was prepared by the method of Example 5 part (iv) using the product of Example 5 part (iv) and 3-chlorobenzenethiol (0.34 g).
APCI– [M–H] 453/455 ii) 3-[(3-chlorophenyl)thio]-2-methyl-5-[(methylsulfonyl)amino]-1H-indole-1-acetic acid The title compound was prepared by the method of Example 5 part (v) using the product from Example 6 part (i).
$^1$H NMR (DMSO-d6) δ 13.25 (s, 1H), 9.33 (s, 1H), 7.46 (d, 1H), 7.21 (m, 2H), 7.11 (dd, 1H), 7.07 (dd, 1H), 6.95 (m, 2H), 4.88 (s, 2H), 2.82 (s, 3H), 2.39 (s, 3H). APCI+ [M+H] 425/427 M.pt. 224° C.

EXAMPLE 7

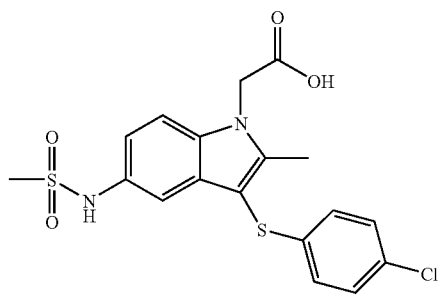

3-[(4-Chlorophenyl)thio]-2-methyl-5-[(methylsulfonyl)amino]-1H-indole-1-acetic acid i) 3-[(4-chlorophenyl)thio]-2-methyl-5-[(methylsulfonyl)amino]-1H-indole-1-acetic acid, ethyl ester The sub-title compound was prepared by the method of Example 5 part (iv) using the product of Example 5 part (iv) and 4-chlorobenzenethiol.
APCI– [M–H] 453/455 ii) 3-[(4-chlorophenyl)thio]-2-methyl-5-[(methylsulfonyl)amino]-1H-indole-1-acetic acid The title compound was prepared by the method of Example 5 part (v) using the product from part (i).
$^1$H NMR (DMSO-d6) δ 13.25 (s, 1H), 9.37 (s, 1H), 7.57 (d, 1H), 7.23 (d, 2H), 7.22 (d, 1H), 7.07 (dd, 1H), 6.96 (d, 2H), 5.11 (s, 2H), 2.82 (s, 3H), 2.39 (s, 3H). APCI+ [M+H] 425/427 M.p. 214° C.

EXAMPLE 8

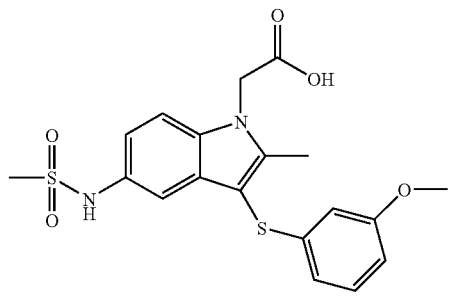

3-[(3-Methoxyphenyl)thio]-2-methyl-5-[(methylsulfonyl)amino]-1H-indole-1-acetic acid i) 3-[(3-methoxyphenyl)thio]-2-methyl-5-[(methylsulfonyl)amino]-1H-indole-1-acetic acid, ethyl ester The sub-title compound was prepared by the method of Example 5 part (iv) using the product of Example 5 part (iv) and 3-methoxybenzenethiol
APCI– [M–H] 449 ii) 3-[(3-methoxyphenyl)thio]-2-methyl-5-[(methylsulfonyl)amino]-1H-indole-1-acetic acid The title compound was prepared by the method of Example 5 part (v) using the product from part (i).

$^1$H NMR (DMSO-d6) δ 13.25 (s, 1H), 9.34 (s, 1H), 7.50 (d, 1H), 7.26, d, 1H), 7.08 (t, 1H), 7.06 (dd, 1H), 6.64 (dd, 1H), 6.55 (d, 1H), 6.47 (d, 1H), 5.11 (s, 2H), 3.62 (s, 3H), 2.82 (s, 3H), 2.40 (s, 3H). APCI– [M–H] 421 M.p. 292° C.

EXAMPLE 9

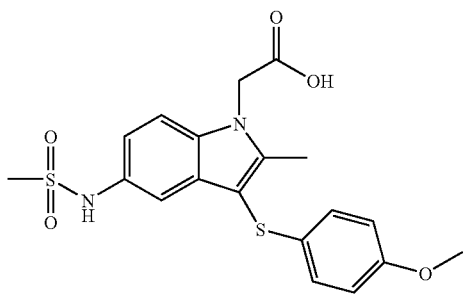

3-[(4-Methoxyphenyl)thio]-2-methyl-5-[(methylsulfonyl)amino]-1H-indole-1-acetic acid i) 3-[(4-methoxyphenyl)thio]-2-methyl-5-[(methylsulfonyl)amino]-1H-indole-1-acetic acid ethyl ester The sub-title compound was prepared by the method of Example 5 part (iv) using the product of Example 5 part (iv) and 4-methoxybenzenethiol.

APCI– [M–H] 449 ii) 3-[(4-methoxyphenyl)thio]-2-methyl-5-[(methylsulfonyl)amino]-1H-indole-1-acetic acid The title compound was prepared by the method of Example 5 part (v) using the product from part (i).

$^1$H NMR (DMSO-d6) δ 13.25 (s, 1H), 9.33 (s, 1H), 7.46 (d, 1H), 7.03 (d, 1H), 7.04 (dd, 1H), 7.00 (d, 2H), 6.81 (d, 2H), 5.07 (s, 2H), 3.67 (s, 3H), 2.83 (s, 3H), 2.42 (s, 3H). APCI+ [M+H] 421 M.p. 215° C.

EXAMPLE 10

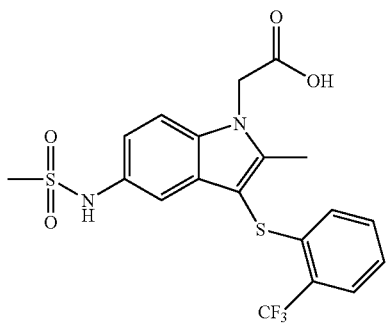

3-[(2-Trifluoromethylphenyl)thio]-2-methyl-5-[(methylsulfonyl)amino]-1H-indole-1-acetic acid i) 3-[(2-trifluoromethylphenyl)thio]-2-methyl-5-[methylsulfonyl)amino]-1H-indole-1-acetic acid, ethyl ester The sub-title compound was prepared by the method of Example 5 part (iv) using the product of Example 5 part (iv) and 2-trifluoromethylbenzenethiol.

APCI– [M–H] 487 ii) 3-[(2-trifluoromethylphenyl)thio]-2-methyl-5-[(methylsulfonyl)amino]-1H-indole-1-acetic acid The title compound was prepared by the method of Example 5 part (v) using the product from part (i).

$^1$H NMR (DMSO-d6) δ 13.25 (s, 1H), 9.35 (s, 1H), 7.72 (d, 1H), 7.54 (d, 1H), 7.36 (t, 1H), 7.24 (t, 1H), 7.22 (s, 1H), 7.11 (dd, 1H), 6.73 (d, 1H), 5.12 (s, 2H), 2.82 (s, 3H), 2.40 (s, 3H). APCI– [M–H] 459 M.p. 207° C.

EXAMPLE 11

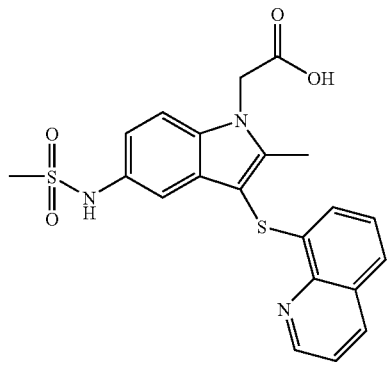

3-[(8-Quinolinyl)thio]-2-methyl-5-[(methylsulfonyl)amino]-1H-indole-1-acetic acid i) 3-[(8-quinolinyl)thio]-2-methyl-5-[(methylsulfonyl)amino]-1H-indole-1-acetic acid, ethyl ester The sub-title compound was prepared by the method of Example 5 part (iv) using the product of Example 5 part (iv) and 8-quinolinthiol.

APCI– [M–H] 470 ii) 3-[(8-quinolinyl)thio]-2-methyl-5-[(methylsulfonyl)amino]-1H-indole-1-acetic acid The title compound prepared by the method of Example 5 part (v) using the product from part (i).

$^1$H NMR (DMSO-d6) δ 13.25 (s, 1H), 9.29 (s, 1H), 8.99 (dd, 1H), 8.38 (d, 1H), 7.65 (m, 2H), 7.54 (d, 1H), 7.30 (t, 1H), 7.20 (s, 1H), 7.11 (dd, 1H), 6.68 (d, 1H), 5.14 (s, 2H), 2.80 (s, 3H), 2.40 (s, 3H). APCI+ [M+H] 442 M.p. 257° C.

EXAMPLE 12

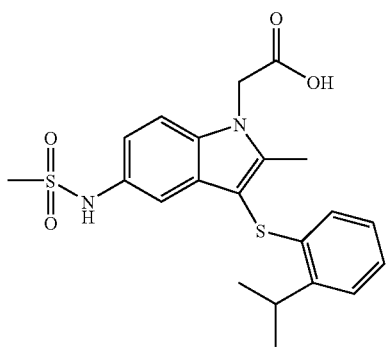

3-[(2-(Methylethyl)phenyl)thio]-2-methyl-5-[(methylsulfonyl)amino]-1H-indole-1-acetic acid i) 3-[(2-(2-methylethyl)phenyl)thio]-2-methyl-5-[(methylsulfonyl)amino]-1H-indole-1-acetic acid, ethyl ester The sub-title compound was prepared by the method of Example 5 part (iv) using the product of Example 5 part (iv) and 2-(2-methylethyl)benzenethiol.
APCI− [M−H] 461 ii) 3-[(2-(2-methylethyl)phenyl)thio]-2-methyl-5-[(methylsulfonyl)amino]-1H-indole-1-acetic acid The title compound was prepared by the method of Example 5 part (v) using the product from part (i).
$^1$H NMR (DMSO-d6) δ 13.25 (s, 1H), 9.33 (s, 1H), 7.49 (d, 1H), 7.27 (d, 1H), 7.22 (d, 1H), 7.06 (m, 2H), 6.89 (t, 1H), 6.50 (dd, 1H), 5.10 (s, 2H), 3.50 (m, 1H), 2.81 (s, 3H), 2.39 (s, 3H), 1.33 (s, 3H), 1.31 (s, 3H). APCI+ [M+H] 433 M.p. 160° C.

EXAMPLE 13

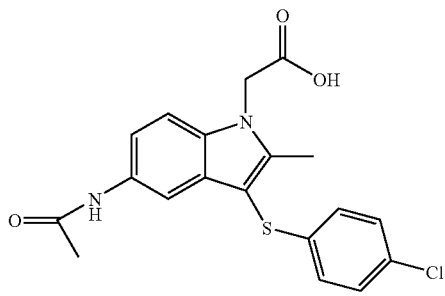

5-(Acetylamino)-3-[(4-chlorophenyl)thio]-2-methyl-1H-indole-1-acetic acid i) 5-(acetylamino)-2-methyl-1H-indole-acetic acid, ethyl ester Acetyl chloride (0.10 g) was added to a solution of the product from Example 5 part ii) (0.28 g) in dichloromethane (10 ml) and triethylamine (0.2 ml) at 0° C. and left to stir at 20° C. for 1 hour. Water was added and the mixture extracted with dichloromethane, dried (Na$_2$SO$_4$) and purified by column chromatography (eluting with 1:1 iso-hexane/ethyl acetate) to give the sub-title compound as a pink powder (0.19 g).
$^1$H NMR (DMSO-d6) δ 9.69 (s, 1H), 7.73 (d, 1H), 7.22 (d, 1H), 7.12 (dd, 1H), 6.18 (s, 1H), 5.00 (s, 2H), 4.13 (q, 2H), 2.30 (s, 3H), 2.02 (s, 3H), 1.20 (t, 3H). APCI− [M−H] 275 ii) 5-(acetylamino)-3-[(4-chlorophenyl)thio]-2-methyl-1H-indole-acetic acid, ethyl ester The sub-title compound was prepared by the method of Example 5 part (iv) using the product from part (i) (0.19 g) and 4-chlorobenzenethiol (0.20 g). The mixture was poured into aqueous sodium thiosulphate, extracted with ethyl acetate, washed with water, dried (Na$_2$SO$_4$) and evaporated. The residue was recrystallised from ethanol to give the sub-title compound as a pink solid (0.13 g).
$^1$H NMR (DMSO-d6) δ 9.80 (s, 1H), 7.67 (d, 1H), 7.43 (d, 1H), 7.36 (dd, 1H), 7.27 (d, 2H), 6.94 (d, 2H), 5.20 (s, 2H), 4.16 (q, 2H), 2.39 (s, 3H), 1.98 (s, 3H), 1.21 (t, 3H). APCI− [M−H] 417/419 iii) 5-(acetylamino)-3-[(4-chlorophenyl)thio]-2-methyl-1H-indole-acetic acid

The title compound was prepared by the method of Example 5 part (v) using the product from part (ii).
$^1$H NMR (DMSO-d6) δ 13.25 (s, 1H), 9.79 (s, 1H), 7.67 (d, 1H), 7.42 (d, 1H), 7.34 (dd, 1H), 7.27 (d, 2H), 6.96 (d, 2H), 5.07 (s, 2H), 2.39 (s, 3H), 1.98 (s, 3H). APCI+ [M+H] 389/391 M.p. 247° C.

EXAMPLE 14

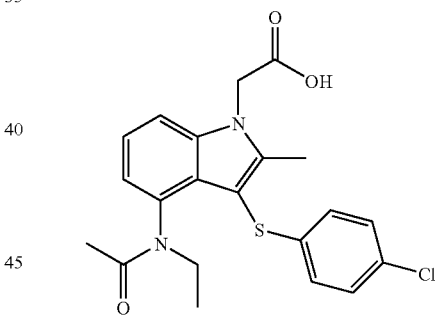

4-(Acetylethylamino)-3-[(4-chlorophenyl)thio]-2-methyl-1H-indole-1-acetic acid i) 3-[(4-chlorophenyl)thio]-4-(ethylamino)-2-methyl-1H-indole-1-acetic acid, ethyl ester The sub-title compound was prepared by the method of Example 1 part (iv) using the by-product from Example 1 part (iii).
$^1$H NMR (DMSO-d6) δ 7.53 (d, 1H), 7.22-7.18 (m, 3H), 6.91-6.87 (m, 3H), 5.21 (s, 2H), 4.19 (q, 2H), 4.01 (m, 1H), 2.92-2.81 (m, 1H), 2.41 (s, 3H), 1.31 (s, 3H), 1.21 (t, 3H), 0.91 (t, 3H)

ii) 4-(acetylethylamino)-3-[(4-chlorophenyl)thio]-2-methyl-1H-indole-1-acetic acid The title compound was prepared by the method of Example 1 part (v) and the product from part (i).

¹H NMR (DMSO-d6) δ 7.55 (d, 1H), 7.22 (dt, 2H), 7.18 (t, 1H), 6.89-6.86 (m, 3H), 4.99 (s, 2H), 2.77 (m, 1H), 4.02 (m, 1H), 2.39 (s, 3H), 1.28 (s, 3H), 0.91 (t, 3H). APCI+ [M+H] 417

EXAMPLE 15

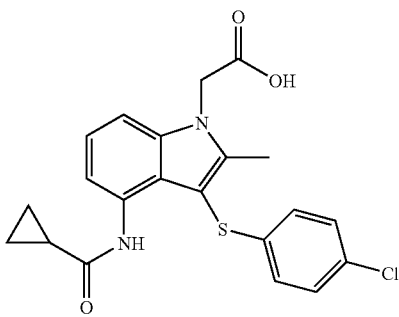

3-[(4-Chlorophenyl)thio]-4-[cyclopropylcarbonyl)amino]-2-methyl-1H-indole-1-acetic acid i) 3-[(4-chlorophenyl)thio]-4-[cyclopropylcarbonyl)amino]-2 methyl-1H-indole-1-acetic acid, ethyl ester The sub-title compound was prepared by the method of Example 1 part (iv) using the product from Example 1 part (iii) and cyclopropylcarbonyl chloride.

¹H NMR (DMSO-d6) δ 9.74 (s, 1H), 7.49 (d, 1H), 7.43-7.26 (m, 3H), 7.10 (t, 1H), 6.98 (m, 2H), 5.24 (s, 2H), 4.18 (q, 2H), 2.40 (s, 3H), 1.53 (m, 1H), 1.18 (t, 3H), 0.64 (m, 4H).

ii) 3-[(4-chlorophenyl)thio]-4-[cyclopropylcarbonyl)amino]-2-methyl-1H-indole-1-acetic acid The sub-title compound was prepared using the method of Example 1 part (v) and the product from part (i).

¹H NMR (DMSO-d6) δ 9.58 (s, 1H), 7.60 (d, 1H), 7.28-7.22 (m, 3H), 7.09 (t, 1H), 7.02 (m, 2H), 5.03 (s, 2H), 2.41 (s, 3H), 1.50 (m, 1H), 0.68 (m, 4H) APCI- [M-H] 413 M.p. 183-185° C.

EXAMPLE 16

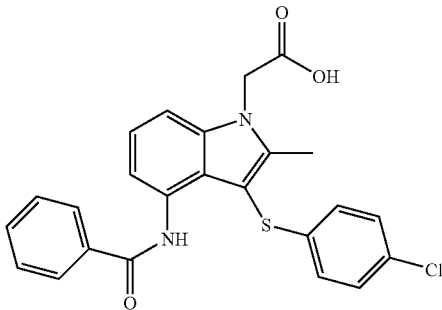

4-(Benzoylamino)-3-[(4-chlorophenyl)thio]-2-methyl-1H-indole-1-acetic acid i) 4-(benzoylamino)-3-[(4-chlorophenyl)thio]-2-methyl-1H-indole-1-acetic acid, ethyl ester The sub-title compound was prepared by the method of Example 1 part (iv) using the product from Example 1 part (iii) and benzoyl chloride.

¹H NMR (DMSO-d6) δ 10.25 (s, 1H), 7.84 (d, 1H), 7.75 (m, 2H), 7.59 (m, 1H), 7.50 (m, 2H), 7.40 (d, 1H), 7.21 (m, 3H), 6.88 (m, 2H), 5.28 (s, 2H), 4.19 (q, 2H), 2.40 (s, 3H), 1.17 (t, 3H).

ii) 4-(benzoylamino)-3-[(4-chlorophenyl)thio]-2-methyl-1H-indole-1-acetic acid

The title compound was prepared using the method of Example 1 part (v) and the product from part (i).

¹H NMR (DMSO-d6) δ 10.26 (s, 1H), 7.86 (d, 1H), 7.75 (dt, 2H), 7.58 (m, 1H), 7.50 (m, 2H), 7.36 (dd, 1H), 7.21 (dt, 2H), 7.17 (t, 1H), 6.90 (dt, 2H), 5.03 (s, 2H), 2.40 (s, 3H). APCI- [M-H] 449 M.pt 213-215° C.

EXAMPLE 17

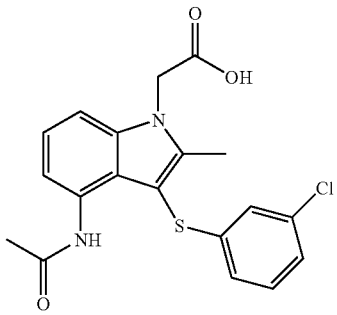

4-(Acetylamino)-3-[(3-chlorophenyl)thio]-2-methyl-1H-indole-1-acetic acid i) 4-(acetylamino)-2-methyl-1H-indole-1-acetic acid, ethyl ester Thiosalicylic acid was added to a solution of the product from Example 1 part (iv) (474 mg) in trifluoroacetic acid (10 ml) was added thiosalicylic acid (351 mg) and the resulting suspension was heated to 60° C. for 4 hours. The mixture was concentrated in vacuo and the residue dissolved in EtOAc and washed with NaHCO₃ (aq), brine, dried (MgSO₄) and evaporated to give crude material. Purification by column chromatography (50% EtOAc/hexane as eluent) gave the sub-title compound (0.13 g).

¹H NMR (DMSO-d6) δ 9.51 (s, 1H), 7.54 (d, 1H), 7.07 (d, 1H), 6.96 (t, 1H), 6.50 (s, 1H), 5.02 (s, 2H), 4.14 (q, 2H), 2.33 (d, 3H), 2.12 (s, 3H), 1.20 (t, 3H).

ii) 4-(acetylamino)-3-[(3-chlorophenyl)thio]-2-methyl-1H-indole-1-acetic acid

The sub-title compound was prepared by the method of Example 5 part (iv) using the product from part (i) (0.11 g) and 3-chlorobenzenethiol (0.048 g), then purified by preparative hplc (eluent MeCN/NH₃ (aq)) to give the title compound (70 mg).

¹H NMR (DMSO-d6) δ 9.49 (s, 1H), 7.43 (d, 1H), 7.29 (d, 1H), 7.24 (t, 1H), 7.14 (dd, 1H), 7.08 (t, 1H), 6.97-6.95 (m, 2H), 4.96 (s, 2H), 2.38 (s, 3H), 1.86 (s, 3H). APCI- [M-H] 387

EXAMPLE 18

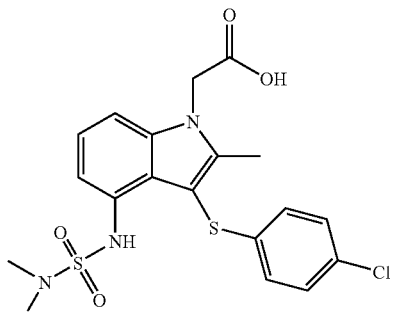

3-[(4-Chlorophenyl)thio]-4-[[(dimethylamino)sulfonyl]amino]-2-methyl-1H-indole-1-acetic acid i) 3-[(4-chlorophenyl)thio]-4-[[(dimethylamino)sulfonyl]amino]-2-methyl-1H-indole-1-acetic acid ethyl ester Triethylamine (55 µl) and dimethylsulfamoyl chloride (43 µl) were added to a solution of the product from Example 1 part (iv) (150 mg) in acetonitrile (5 ml). The mixture was heated at reflux for 24 hours, adsorbed onto silica and purified using column chromatography (33% EtOAc/hexane as eluent) to give the sub-title compound (95 mg).

$^1$H NMR (DMSO-d6) δ 8.80 (s, 1H), 7.35-7.29 (m, 3H), 7.13 (t, 1H), 7.07 (dd, 1H), 6.99 (dt, 2H), 5.25 (s, 2H), 4.18 (q, 2H), 2.56 (s, 6H), 2.37 (s, 3H), 1.21 (t, 3H).

ii) 3-[(4-chlorophenyl)thio]-4-[[(dimethylamino)sulfonyl]amino]-2-methyl-1H-indole-1-acetic acid The title compound was prepared using the method of Example 1 part (v) and the product from part (i).

$^1$H NMR (DMSO-d6) δ 8.79 (s, 1H), 7.31 (m, 2H), 7.14 (dd, 1H), 7.04-6.99 (m, 4H), 4.51 (s, 2H), 2.54 (s, 6H), 2.34 (s, 3H). APCI– [M–H] 452

EXAMPLE 19

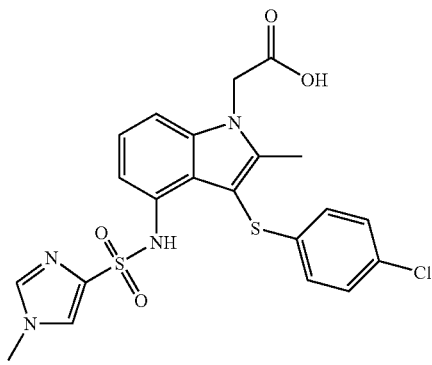

3-[(4-Chlorophenyl)thio]-2-methyl-4-[[(1-methyl-1H-imidazol-4-yl)sulfonyl]amino]-1H-indole-1-acetic acid i) 3-[(4-chlorophenyl)thio]-2-methyl-4-[[(1-methyl-1H-imidazol-4-yl)sulfonyl]amino]-1H-indole-1-acetic acid, ethyl ester Triethylamine (75 µl) and 1-methyl-1H-imidazolesulfonyl chloride (96 mg) were added to a solution of the product from Example 1 part (iii) (0.2 g) in acetonitrile (20 ml) and the mixture was heated at reflux overnight, cooled, adsorbed onto silica and purified using column chromatography (70% EtOAc/hexane as eluent) to give the sub-title compound as an oil (245 mg).

$^1$H NMR (DMSO-d6) δ 9.17 (s, 1H), 7.73 (d, 1H), 7.63 (d, 1H), 7.32 (dt, 2H), 7.24 (dd, 1H), 7.08-7.02 (m, 2H), 6.98 (dt, 2H), 5.20 (s, 2H), 4.15 (q, 2H), 3.60 (s, 3H), 2.33 (s, 3H), 1.17 (t, 3H).

ii) 3-[(4-chlorophenyl)thio]-2-methyl-4-[[(1-methyl-1H-imidazol-4-yl)sulfonyl]amino]-1H-indole-1-acetic acid The title compound was prepared using the method of Example 1 part (v) and the product from part (i).

$^1$H NMR (DMSO-d6) δ 9.16 (s, 1H), 7.73 (d, 1H), 7.62 (d, 1H), 7.31 (dt, 2H), 7.22 (dd, 1H), 7.08-7.02 (m, 2H), 6.99 (dt, 2H), 5.01 (s, 2H), 3.59 (s, 3H), 2.32 (s, 3H). APCI– [M–H] 489

EXAMPLE 20

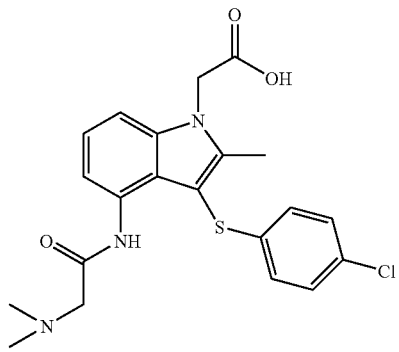

3-[(4-Chlorophenyl)thio]-4-[[(dimethylamino)acetyl]amino]-2-methyl-1H-indole-1-acetic acid i) 3-[(4-chlorophenyl)thio]-4-[[(dimethylamino)acetyl]amino]-2-methyl-1H-indole-1-acetic acid, ethyl ester The sub-title compound was prepared by the method of Example 1 part (iv) using the product from Example 1 part (iii) and (dimethylamino)-acetyl chloride, hydrochloride. The product was purified using column chromatography (33% EtOAc/hexane as eluent).

$^1$H NMR (DMSO-d6) δ 10.77 (s, 1H), 8.15 (d, 1H), 7.35-7.27 (m, 3H), 7.13 (t, 1H), 6.97 (d, 2H), 5.25 (s, 2H), 4.17 (q, 2H), 2.94 (s, 2H), 2.38 (s, 3H), 2.10 (s, 6H), 1.21 (t, 3H).

ii) 3-[(4-chlorophenyl)thio]-4-[[(dimethylamino)acetyl]amino]-2-methyl-1H-indole-1-acetic acid The title compound was prepared using the method of Example 1 part (v) and the product from part (i).

$^1$H NMR (DMSO-d6) δ 10.76 (s, 1H), 8.10 (d, 1H), 7.30 (dt, 2H), 7.17 (d, 1H), 7.05 (t, 1H), 6.98 (dd, 2H), 4.66 (s, 2H), 2.93 (s, 2H), 2.35 (s, 3H), 2.09 (s, 6H). APCI– [M–H] 430

EXAMPLE 21

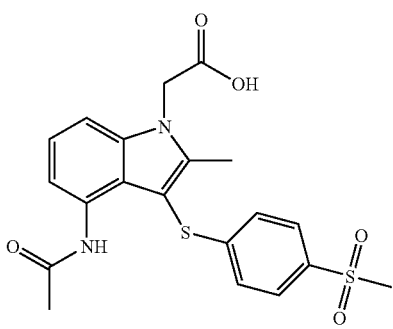

4-(Acetylamino)-2-methyl-3-[[4-(methylsulfonyl)phenyl]thio]-1H-indole-1-acetic acid i) 4-(methylsulfonyl)benzenethiol 1-fluoro-4-(methylsulfonyl)benzene and sodium bisulphide (10 g) were heated in NMP (10 ml) at 80° C. for 2 h. The mixture was poured into water, washed with EtOAc, acidified with concentrated hydrochloric acid and extracted with EtOAc. The organics were washed with water, dried (MgSO$_4$) and evaporated to give the sub-title compound, which was used in the next step without characterisation.

ii) 4-(acetylamino)-2-methyl-3-[[(methylsulfonyl)phenyl]thio]-1H-indole-1-acetic acid, ethyl ester The sub-title compound was prepared by the method of Example 5 part (iv) using the product from part (i) and the product from Example 17 part (i), and purified by chromatography (50% EtOAc/hexane increasing to 66% EtOAc/hexane as eluent) to give the sub-title compound.

$^1$H NMR (DMSO-d6) δ 9.45 (s, 1H), 7.72 (dt, 2H), 7.38 (d, 1H), 7.32 (d, 1H), 7.16-7.11 (m, 3H), 5.27 (s, 2H), 4.19 (q, 2H), 3.14 (s, 3H), 2.38 (s, 3H), 1.82 (s, 3H), 1.22 (t, 3H).

iv) 4-(acetylamino)-2-methyl-3-[[4-(methylsulfonyl)phenyl]thio]-1H-indole-1-acetic acid The title compound was prepared using the method of Example 1 part (v) and the product from part (ii).

$^1$H NMR (DMSO-d6) δ 9.44 (s, 1H), 7.72 (dd, 2H), 7.38 (d, 1H), 7.31 (d, 1H), 7.17-7.10 (m, 3H), 5.14 (s, 2H), 3.14 (s, H), 2.38 (s, 3H), 1.82 (s, 3H). APCI– [M–H] 431

EXAMPLE 22

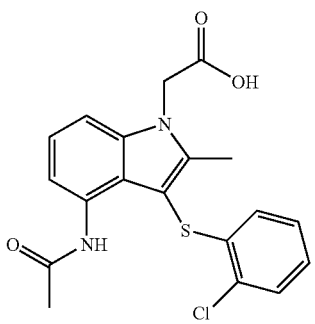

4-(Acetylamino)-3-[(2-chlorophenyl)thio]-2-methyl-1H-indole-1-acetic acid 4-(acetylamino)-3-[(2-chlorophenyl)thio]-2-methyl-1H-indole-1-acetic acid The title compound was prepared by the method of Example 5 parts (iv) and using the product from Example 17 part (i) and 2-chlorothiophenol, and purified by column chromatography (33% EtOAc/hexane as eluent). The resulting product was treated as outlined in example 1 part (v) to give the title compound.

$^1$H NMR (DMSO-d6) δ 9.43 (s, 1H), 7.46 (dd, 1H), 7.37 (dd, 2H), 7.14-7.05 (m, 3H), 6.42 (dd, 1H), 5.14 (s, 2H), 2.37 (s, 3H), 1.81 (s, 3H) APCI+ [M+H] 389

EXAMPLE 23

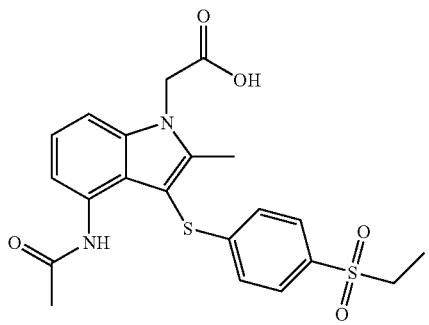

4-(Acetylamino)-2-methyl-3-[[4-(ethylsulfonyl)phenyl]thio]-1H-indole-1-acetic acid i) 4-(acetylamino)-2-methyl-3-[[4-(ethylsulfonyl)phenyl]thio]-1H-indole-1-acetic acid The title compound was prepared by the method of Example 5 part (iv) using the product from Example 17 part (i) and 4-(ethylsulfonyl)benzenethiol. The product was purified by preparative hplc (eluent MeCN/NH$_3$ (aq)).

$^1$H NMR (DMSO-d6) δ 9.41 (s, 1H), 7.66 (d, 2H), 7.30 (d, 2H), 7.17 (d, 2H), 7.08 (t, 1H), 4.85 (s, 2H), 3.20 (q, 2H), 2.37 (s, 3H), 1.78 (s, 3H), 1.05 (t, 3H). APCI– [M–H] 445

EXAMPLE 24

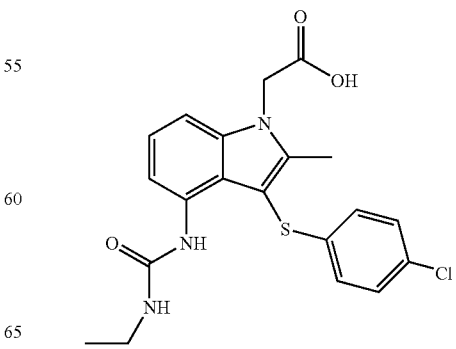

3-[(4-Chlorophenyl)thio]-4-[[(ethylamino)carbonyl]amino]-2-methyl-1H-indole-1-acetic acid i) 3-[(4-chlorophenyl)thio]-4-[[(ethylamino)carbonyl]amino]-2-methyl-1H-indole-1-acetic acid, ethyl ester Ethyl isocyanate (32 μl) was added to a solution of the product from Example 1 part (iii) (150 mg) in dichloromethane (10 ml). The reaction was stirred at room temperature for 4 days before heating at reflux for 24 hours. The mixture was adsorbed onto silica and purified using column chromatography (33% EtOAc/hexane increasing to 50% EtOAc/hexane as eluent) to give sub-title compound (150 mg).

$^1$H NMR (DMSO-d6) δ 8.37 (s, 1H), 7.57 (d, 1H), 7.28 (dt, 2H), 7.12 (dd, 1H), 7.06-6.98 (m, 3H), 6.81 (t, 1H), 5.19 (s, 2H), 4.17 (q, 2H), 2.98 (dt, 2H), 2.37 (s, 3H), 1.21 (t, 3H), 0.96 (t, 3H)

ii) 3-[(4-chlorophenyl)thio]-4-[[(ethylamino)carbonyl]amino]-2-1H-indole-1-acetic acid The title compound was prepared using the method of Example 1 part (v) and the product from part (i).

$^1$H NMR (DMSO-d6) δ 8.39 (s, 1H), 7.53 (dd, 1H), 7.26 (dt, 2H), 7.04-6.94 (m, 4H), 6.76 (t, 1H), 4.56 (s, 2H), 2.98 (dt, 2H), 2.34 (s, 3H), 0.95 (t, 3H). APCI+ [M+H] 418

EXAMPLE 25

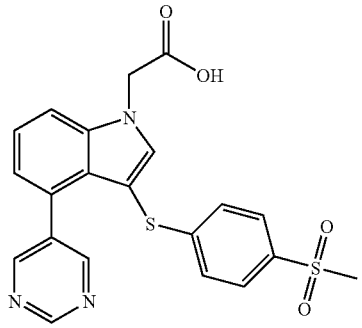

3-[[4-(Methylsulfonyl)phenyl]thio]-4-(5-pyrimidinyl)-1H-indole-1-acetic acid i) 4-bromo-3-[[4-(methylsulfonyl)phenyl]thio]-1H-indole The sub-title compound was prepared by the method of Example 5 part (iv) using the product from Example 21 part (i) (0.89 g) and 4-bromoindole (0.96 g). The residue was purified by chromatography (50% EtOAc/hexane as eluent) to give the sub-title compound (1.3 g).

$^1$H NMR (DMSO-d6) δ 12.18 (s, 1H), 7.93 (s, 1H), 7.73 (d, 2H), 7.56 (d, 1H), 7.29 (d, 1H), 7.17 (d, 2H), 7.12 (t, 1H), 3.14 (s, 3H)

ii) 4-bromo-3-[[4-(methylsulfonyl)phenyl]thio]-1H-indole-1-acetic acid

Sodium t-butoxide (1.37 g) was added to a solution of the product from part (i) (2.4 g) in DMF (20 ml) and the mixture stirred for 15 minutes. Ethyl bromoacetate (0.86 ml) was added and the mixture stirred for a further 30 minutes. 1M sodium hydroxide (10 ml) was then added and the mixture stirred for 2 hours. The mixture was diluted with water (200 ml), washed with EtOAc (50 ml), acidified with 2M hydrochloric acid and the resulting solid filtered off and dried to give the sub-titled compound (2.5 g).

$^1$H NMR (DMSO-d6) δ 7.86 (s, 1H), 7.73 (d, 2H), 7.50 (d, 1H), 7.28 (d, 1H), 7.19 (d, 2H), 7.11 (t, 1H), 4.73 (s, 2H), 3.14 (s, 3H)

iii) 3-[[4-(methylsulfonyl)phenyl]thio]-4-(5-pyrimidinyl)-1H-indole-1-acetic acid The product from part (ii) (0.4 g), phenylboronic acid (0.17 g), tetrakis(triphenylphosphine) palladium (100 mg) and 2M aqueous sodium hydrogen carbonate (2 ml) were dissolved in ethanol (10 ml) and heated at reflux for 8 hours. The mixture was cooled to room temperature, diluted with EtOAc (100 ml), washed with water and brine. The organic solution was dried (MgSO$_4$), filtered and evaporated in vacuo and the residue purified by hplc to give the title compound (190 mg).

$^1$H NMR (DMSO-d6) δ 8.93 (s, 1H), 8.58 (s, 1H), 7.93 (s, 1H), 7.70 (d, 1H), 7.52 (d, 2H), 7.37 (t, 1H), 7.03 (d, 1H), 6.70 (d, 2H), 5.15 (s, 2H), 3.12 (s, 3H) APCI− [M−H] 438

EXAMPLE 26

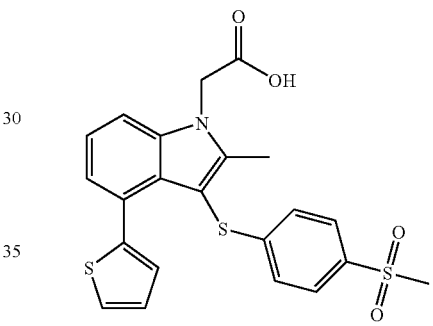

2-Methyl-3-[[4-(methylsulfonyl)phenyl]thio]-4-(2-thiophenyl)-1H-indole-1-acetic acid i) 1-[[4-(methylsulfonyl)phenyl]thio]acetone The product from Example 21 part (i) (3.4 g) was dissolved in acetone (100 ml), potassium carbonate (3.0 g) added, followed by the dropwise addition of chloroacetone (1.5 ml). The mixture was stirred at room temperature for 20 hours, concentrated, partitioned between EtOAc and water, dried (MgSO$_4$) and evaporated. The residue was purified by chromatography (50% EtOAc/hexane as eluent) to give the sub-title compound (2.6 g).

$^1$H NMR (400 MHz, CDCl$_3$) δ 7.84 (d, 2H), 7.43 (d, 2H), 3.81 (s, 2H), 3.06 (s, 3H), 2.34 (s, 3H) APCI− [M−H] 243 M.p. 95-7° C.

ii) 4-bromo-2-methyl-3-[[4-(methylsulfonyl)phenyl]thio]-1H-indole

The sub-title compound was prepared by the method of Example 3 part (i) using the product from part (i) (1.6 g) and 3-bromophenyl hydrazine hydrochloride (1.47 g). The product was purified by using chromatography (30% EtOAc/hexane as eluent) to give the sub-title compound (0.5 g).

$^1$H NMR (CDCl$_3$) δ 8.41 (s, 1H), 7.68 (d, 2H), 7.54 (s, 1H), 7.32 (d, 1H), 7.25 (d, 1H), 7.10 (d, 2H), 3.00 (s, 3H), 2.50 (s, 3H) APCI− [M−H] 394 iii) 4-bromo-2-methyl-3-[[4-(methylsulfonyl)phenyl]thio]-1H-indole-1-acetic acid, 1,1-dimethylethyl ester The sub-title compound was prepared by the method of Example 1 part (ii) using the product of part (i) and t-butyl-bromoacetate. The product was purified using chromatography (50% EtOAc/hexane as eluent) to give the sub-title compound (0.5 g).

APCI+ [M+H] 510 iv) 2-methyl-3-[[4-(methylsulfonyl)phenyl]thio]-4-(2-thiophenyl)-1H-indole-1-acetic acid, 1,1-dimethylethyl ester A mixture of palladium acetate (24 mg), tri-ortho tolylphosphine (64 mg) and methanol (6 ml) were stirred under nitrogen for 10 minutes. The product of part (ii) in methanol (10 ml) was added, followed by sodium carbonate (1.12 g) and thiophene-2-boronic acid (0.68 g). After stirring for 45 minutes at 80° C. further palladium acetate (24 mg) and tri-ortho tolylphosphine (64 mg) in methanol (1 ml) was added, followed by thiophene-2-boronic acid (0.2 g) and toluene (5 ml), the reaction mixture was stirred at 80° C. for 1 hour. The reaction mixture was concentrated in vacuo, water was added and the mixture extracted with dichloromethane. The organic layer was dried (MgSO$_4$) then concentrated in vacuo. The residue was dissolved in methanol and treated with sodium hydroxide (5 ml). After one hour the reaction mixture was concentrated in vacuo, then purified by reverse phase HPLC to give the title compound (160 mg).

$^1$H NMR (DMSO-d6) δ 7.58 (m, 3H), 7.38 (d, 1H), 7.18 (t, 1H), 6.99 (d, 1H), 6.87 (m, 3H), 6.78 (s, 1H), 4.98 (s, 2H), 3.11 (s, 3H), 2.38 (s, 3H) APCI– [M–H] 456

EXAMPLE 27

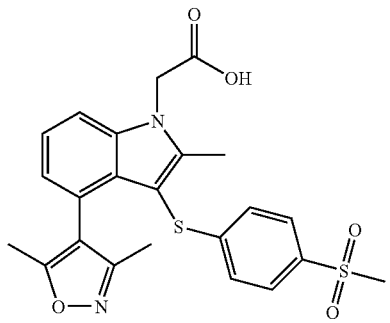

4-(3,5-Dimethyl-4-isoxazolyl)-2-methyl-3-[[4-(methylsulfonyl)phenyl]thio]-1H-indole-1-acetic acid Prepared by the method of Example 26 part (iv) using the product of Example 26 part (ii) and 3,5-dimethylisoxazolyl-4-boronic acid. The product was purified using reverse phase preparative chromatography (eluent MeCN/NH$_3$(aq)) to give the title compound (6 mg).

$^1$H NMR (DMSO-d6) δ 7.61 (d, 1H), 7.46 (d, 2H), 7.17 (t, 1H), 6.82 (d, 2H), 6.75 (d, 1H), 4.57 (s, 2H), 3.32 (s, 3H), 1.9 (s, 3H), 1.11 (s, 6H) APCI– [M–H] 469

EXAMPLE 28

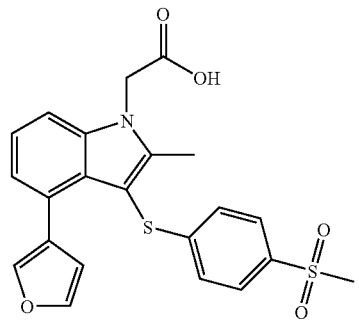

4-(3-Furanyl)-2-methyl-3-[[4-(methylsulfonyl)phenyl]thio]-1H-indole-1-acetic acid i) 4-(3-furanyl)-2-methyl-3-[[4-(methylsulfonyl)phenyl]thio]-1H-indole-1-acetic acid, ethyl ester The sub-title compound was prepared by the method of Example 26 part (iv) using the product of Example 27 part (i) and furan-3-boronic acid. The product was used without characterisation in part (ii).

ii) 4-(3-furanyl)-2-methyl-3-[[4-(methylsulfonyl)phenyl]thio]-1H-indole-1-acetic acid The title compound was prepared by the method of Example 1 part (v) using the product from part (i). The product was purified using hplc (eluent MeCN/NH$_3$(aq)) to give the title compound (60 mg).

$^1$H NMR (DMSO-d6) δ 7.41-7.63 (m, 5H), 7.17 (t, 1H), 6.9-6.96 (m, 3H), 6.36 (s, 1H), 5.18 (s, 2H), 3.18 (s, 3H), 2.4 (s, 3H) APCI– [M–H] 440

EXAMPLE 29

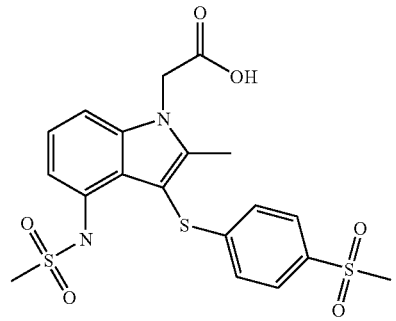

2-Methyl-4-[(methylsulfonyl)amino]-3-[[4-(methylsulfonyl)phenyl]thio]-1H-indole-1-acetic acid i) 2-methyl-4-[(methylsulfonyl)amino]-1H-indole-1-acetic acid Thiosalicylic acid (0.35 g) was added to a solution of the product from Example 2 part (i) (0.47 g) in TFA (10 ml). The mixture was stirred at room temperature for 1 hour and then heated at 60° C. for 4 hours. The TFA was evaporated and the residue dissolved in EtOAc. The organics were washed with aqueous sodium bicarbonate and brine, died (MgSO$_4$) and evaporated. The residue was purified using chromatography (50% EtOAc/hexane as eluent) to give the sub-title compound (0.16 g).

$^1$H NMR (DMSO-d6) δ 9.4 (s, 1H), 7.19 (d, 1H), 6.95-7.04 (m, 2H), 6.53 (d, 1H), 5.04 (s, 2H), 4.15 (q, 2H), 2.91 (s, 3H), 2.32 (d, 3H), 1.21 (t, 3H)

ii) 2-methyl-4-[(methylsulfonyl)amino]-3-[[4-(methylsulfonyl)phenyl]thio]-1H-indole-1-acetic acid, ethyl ester The sub-title compound was prepared by the method of Example 5 part (iv) using the product from part (i) and the product from Example 21 part (i).

$^1$H NMR (DMSO-d6) δ 8.76 (s, 1H), 7.74 (dd, 2H), 7.44 (d, 1H), 7.07-7.21 (m, 4H), 5.29 (s, 2H), 4.19 (q, 2H), 3.14 (s, 3H), 2.76 (s, 3H), 2.36 (s, 3H), 1.22 (t, 3H)

iii) 2-methyl-4-[(methylsulfonyl)amino]-3-[[4-(methylsulfonyl)phenyl]thio]-1H-indole-1-acetic acid The title compound was prepared by the method of Example 1 part (v) using the product from part (ii) and the recrystallised from ethanol to give the title compound as a pale pink solid (75 mg).

$^1$H NMR (DMSO-d6) δ 8.78 (s, 1H), 7.74 (d, 2H), 7.44 (d, 1H), 7.13-7.2 (m, 3H), 7.08 (d, 1H) 5.15 (s, 2H), 3.14 (s, 3H), 2.76 (s, 3H), 2.36 (s, 3H) APCI+ [M+H] 469

EXAMPLE 30

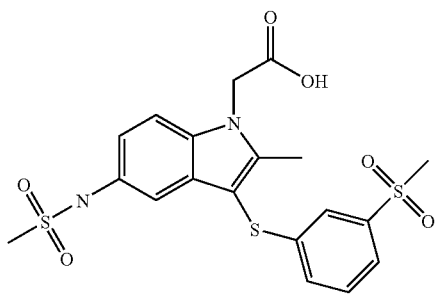

2-Methyl-5-[(methylsulfonyl)amino]-3-[[3-(methylsulfonyl)phenyl]thio]-1H-indole-1-acetic acid i) O-[3-(methylsulfonyl)phenyl]carbamothioic acid, dimethyl ester Sodium hydride (0.33 g) was added to a solution of 3-(methylsulfonyl)phenol in DMF (10 ml) and stirred for 30 minutes. Dimethylcarbamothioic chloride (1.1 g) was added and the reaction heated at 80° C. for 4 hours. The mixture was poured into aqueous ammonium chloride, extracted with EtOAc, washed with water, dried (MgSO$_4$) and evaporated in vacuo. The residue was purified using chromatography (30-50% ether/hexane as eluent) to give the sub-title compound (1.3 g).

$^1$H NMR (DMSO-d6) δ 7.82 (dd, 1H), 7.69 (t, 1H), 7.59 (t, 1H), 7.39 (dd, 1H), 3.47 (s, 3H), 3.37 (s, 3H), 3.08 (s, 3H) APCI+ [M+H] 260 ii) S-[3-(methylsulfonyl)phenyl]carbamothioic acid, dimethyl ester

The product from part (i) (1.1 g) was dissolved in N,N-dimethylaniline (3 ml) and heated at 220° C. for 8 hours. The mixture was cooled, poured into 2M hydrochloric acid and extracted with EtOAc. The organics were washed with 2M hydrochloric acid and water, dried (MgSO$_4$) and evaporated in vacuo. The oily residue was treated with ether to give the sub-title compound as a white solid (0.9 g).

$^1$H NMR (DMSO-d6) δ 8.07 (d, 1H), 7.94 (dd, 1H), 7.79 (dd, 1H), 7.59 (t, 1H), 3.04-3.12 (m, 6H), 3.07 (s, 3H) APCI+ [M+H] 260 iii) 3-(methylsulfonyl)benzenethiol

The product from part (ii) (0.9 g) was suspended in 2M sodium hydroxide (70 ml) and heated at reflux for 1.5 h to give a brown solution. The solution was cooled, extracted with EtOAc, dried (MgSO$_4$) and evaporated to give the sub-title compound (0.45 g).

$^1$H NMR (DMSO-d6) δ 7.84 (m, 1H), 7.7 (m, 1H), 7.52 (m, 1H), 7.44 (t, 1H), 3.67 (s, 1H), 3.06 (s, 3H) APCI− [M−H] 187 iv) 2-methyl-5-[(methylsulfonyl)amino]-3-[[3-(methylsulfonyl)phenyl]thio]-1H-indole acetic acid, ethyl ester The sub-title compound was prepared by the method of Example 5 part (iv) using the product from part (iii) (0.22 g) and the product from Example 5 part (iii) and recrystallised from ethanol.

$^1$H NMR (DMSO-d6) δ 7.58 (m, 2H), 7.34 (m, 2H), 7.18 (t, 2H), 6.28 (s, 1H), 4.89 (s, 2H), 4.25 (q, 2H), 3.06 (s, 3H), 2.96 (s, 3H), 2.49 (s, 3H), 1.28 (t, 3H) APCI+ [M+NH$_4$] 514 M.p. 176-8° C.

v) 2-methyl-5-[(methylsulfonyl)amino]-3-[[3-(methylsulfonyl)phenyl]thio]-1H-indole-1-acetic acid The title compound was prepared by the method of Example 1 part (v) using the product from part (iv). The basic solution was adjusted to pH5 with 0.5M hydrochloric acid and the resulting precipitate filtered off and dried to give the title compound (0.19 g).

$^1$H NMR (DMSO-d6) δ 9.35 (s, 1H), 7.61 (m, 1H), 7.57 (d, 1H), 7.53 (d, 1H), 7.46 (t, 1H), 7.24 (d, 1H), 7.18 (m, 1H), 7.08 (dd, 1H), 5.05 (s, 2H), 3.17 (s, 3H), 2.82 (s, 3H), 2.41 (s, 3H) APCI+ [M+NH$_4$] 469 M.p. 233-6° C.

EXAMPLE 31

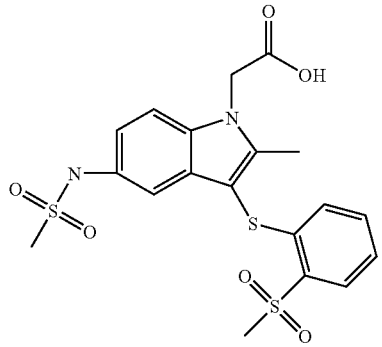

2-Methyl-5-[(methylsulfonyl)amino]-3-[[2-(methylsulfonyl)phenyl]thio]-1H-indole-1-acetic acid i) 1-fluoro-2-(methylsulfonyl benzene A solution of oxone (17 g) in water (85 ml) was added to a solution of 2-fluorothioanisole in acetonitrile (85 ml) and the mixture stirred at room temperature for 20 hours. The mixture was concentrated, extracted with EtOAc, washed with water, dried (MgSO$_4$) and evaporated to give the sub-title compound (5.9 g).

$^1$H NMR (DMSO-d6) δ 7.98 (t, 1H), 7.66 (m, 1H), 7.35 (t, 1H), 7.26 (t, 1H), 3.23 (s, 3H)

ii) 2-(methylsulfonyl)benzenethiol

The sub-title compound was prepared by the method of Example 26 part (i) using the product from part (i) (5.4 g).

$^1$H NMR (DMSO-d6) δ 8.05 (d, 1H), 7.46 (m, 2H), 7.35 (m, 1H), 4.84 (s, 1H), 3.21 (s, 3H) APCI– [M–H] 187 iii) 2-methyl-5-[methylsulfonyl)amino]-3-[[2-(methylsulfonyl)phenyl]thio]-1H-indole-1-acetic acid, ethyl ester The sub-title compound was prepared by the method of Example 5 part (iv) using the product from part (ii) (1.3 g) and the product from Example 5 part (iii) (0.6 g). The product was purified using chromatography (50-67% EtOAc/hexane as eluent) to give the sub-title compound (0.18 g).

$^1$H NMR (DMSO-d6) δ 8.05 (d, 1H), 7.16-7.27 (m, 4H), 6.77 (dd, 1H), 6.33 (s, 1H), 4.9 (s, 2H), 4.26 (q, 2H), 3.44 (s, 3H), 2.88 (s, 3H), 2.5 (s, 3H), 1.21 (t, 3H) APCI+ [M+NH$_4$] 514 M.p. 1747° C.

v) 2-methyl-5-[(methylsulfonyl)amino]-3-[[2-(methyl-sulfonyl)phenyl]thio]-1H-indole-acetic acid Prepared by the method of Example 1 part (v) using the product from part (iii). The basic solution was adjusted to pH5 with 0.5M hydrochloric acid and the resulting precipitate filtered and dried to give the title compound.

$^1$H NR (DMSO-d6) δ 9.38 (s, 1H), 7.92 (dd, 1H), 7.53 (d, 1H), 7.39 (m, 1H), 7.31 (m, 1H), 7.16 (d, 1H), 7.10 (dd, 1H), 6.75 (dd, 1H), 5.11 (s, 2H), 3.51 (s, 3H), 2.81 (s, 3H), 2.41 (s, 3H). APCI+ [M+NH$_4$] 486 M.p. 227-30° C.

EXAMPLE 32

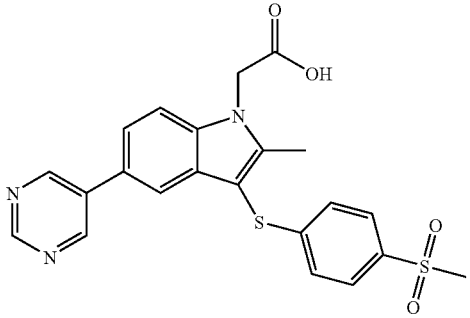

2-Methyl-3-[[(4-(methylsulfonyl)phenyl]thio]-5-(5-pyrimidinyl)-1H-indole-1-acetic acid i) 5-bromo-2-methyl-3-[[4-(methylsulfonyl)phenyl]thio]-1H-indole The sub-title compound was prepared by the method of Example 3 part (i) using the product from Example 26 part (i) (2.5 g) and 4-bromophenyl hydrazine hydrochloride (2.3 g). The reaction mixture was evaporated to half volume and the resulting precipitate filtered off, washed with ether and dried to yield the sub-title compound (2.2 g).

$^1$H NMR (DMSO-d6) δ 12.04 (s, 1H), 7.73 (d, 2H), 7.4 (m, 2H), 7.27 (dd, 1H), 7.14 (d, 2H), 3.14 (s, 3H), 2.45 (s, 3H) APCI– [M–H] 394 ii) 5-bromo-2-methyl-3-[[4-(methylsulfonyl)phenyl]thio]-1H-indole-1-acetic acid, ethyl ester The sub-title compound was prepared by the method of Example 1 part (ii) using the product of part (i) and the product was purified using chromatography (33-50% EtOAc/hexane as eluent).

$^1$H NMR (DMSO-d6) δ 7.71 (d, 2H), 7.64 (d, 1H), 7.34 (dd, 1H), 7.16 (d, 1H), 7.1 (d, 2H), 4.88 (s, 2H), 4.24 (q, 2H), 3.0 (s, 3H), 2.47 (s, 3H) 1.29 (t, 3H) APCI+ [M+H] 482 iii) 2-methyl-3-[[4-(methylsulfonyl)phenyl]thio]-5-(5-pyrimidinyl)-1H-indole-1-acetic acid, ethyl ester The sub-title compound was prepared by the method of Example 3 part (iii) using the product of part (ii) and pyrimidine-5-boronic acid. Carried forward to part (iii) without characterisation.

iv) 2-methyl-3-[[4-(methylsulfonyl)phenyl]thio]-5-(5-pyrimidinyl)-1H-indole-1-acetic acid The title compound was prepared by the method of Example 1 part (v) using the product from part (iii). The basic solution was adjusted to pH5 with 0.5M hydrochloric acid and the resulting precipitate filtered off and dried to give the title compound (21 mg).

$^1$H NMR (DMSO-d6) δ 9.38 (s, 1H), 9.09 (s, 2H), 7.71-7.79 (m, 4H), 7.64 (d, 1H), 7.17 (d, 2H), 5.23 (s, 2H), 3.12 (s, 3H) 2.45 (s, 3H) APCI+ [M+H] 454 M.p.>290° C.

EXAMPLE 33

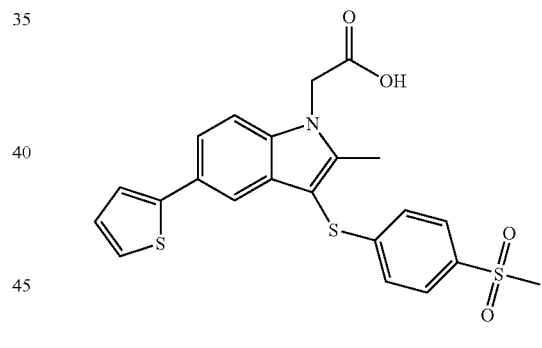

2-Methyl-3-[[4-(methylsulfonyl)phenyl]thio]-5-(2-thiophenyl)-1H-indole-1-acetic acid i) 2-methyl-3-[[4-(methylsulfonyl)phenyl]thio]-5-(3-thiophenyl)-1H-indole-1-acetic acid, ethyl ester The sub-title compound was prepared by the method of Example 3 part (iii) using the product of part (ii) and thiophene-2-boronic acid. Used without further characterisation.

ii) 2-methyl-3-[[4-methylsulfonyl)phenyl]thio]-5-(2-thiophenyl)-1H-indole-1-acetic acid The title compound was prepared by the method of Example 1 part (v) using the product from part (ii). The basic solution was adjusted to pH 5 with 0.5 M hydrochloric acid and the resulting precipitate filtered off and dried, then recrystallised from acetonitrile to give the title compound.

¹H NMR (DMSO-d6) δ 7.72 (d, 2H), 7.63 (d, 1H), 7.53 (m, 2H), 7.42 (d, 1H), 7.39 (t, 1H), 7.18 (d, 2H), 7.08 (m, 1H), 5.15 (s, 2H), 3.13 (s, 3H) 2.42 (s, 3H) APCI+ [M+H] 458

EXAMPLE 34

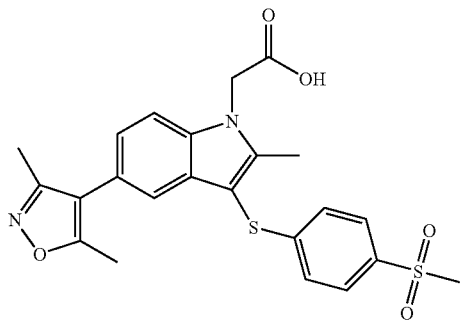

5-(3,5-Dimethyl-4-isoxazolyl)-2-methyl-3-[[4-(methylsulfonyl)phenyl]thio]-1H-indole-1-acetic acid i) 5-(3,5-dimethyl-4-isoxazolyl)-2-methyl-3-[[4-(methylsulfonyl)phenyl]thio]-1H-indole-1-acetic acid ethyl ester The sub-title compound was prepared by the method of Example 3 part (iii) using the product of part (ii) and 3,5-dimethylisoxazolyl-4-boronic acid. Used in the next step without characterisation.

ii) 5-(3,5-dimethyl-4-isoxazolyl)-2-methyl-3-[[4-(methylsulfonyl)phenyl]thio]-1H-indole 1-acetic acid The title compound was prepared by the method of Example 1 part (v) using the product from part (ii). The basic solution was adjusted to pH5 with 0.5M hydrochloric acid and the resulting precipitate filtered, dried and recrystallised from cyclohexane/ethanol to give the title compound.

¹H NMR (DMSO-d6) δ 7.73 (d, 2H), 7.66 (d, 1H), 7.24 (d, 1H), 7.19 (m, 3H), 5.19 (s, 2H), 3.13 (s, 3H) 2.44 (s, 3H), 2.31 (s, 3H), 2.13 (s, 3H) APCI+ [M+H] 471

EXAMPLE 35

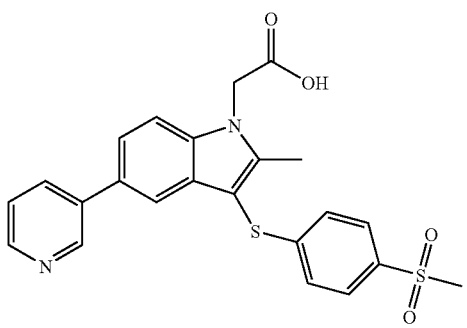

2-Methyl-3-[[4-(methylsulfonyl)phenyl]thio]-5-(3-pyridinyl)-1H-indole-1-acetic acid i) 2-methyl-3-[[4-(methylsulfonyl)phenyl]thio]-5-(3-pyridinyl)-1H-indole-1-acetic acid, ethyl ester The sub-title compound was prepared by the method of Example 3 part (iii) using the product of part (ii) and pyridine-3-boronic acid.

¹H NMR (CDCl₃) δ 8.85 (s, 1H), 8.54 (s, 1H), 7.87 (m, 1H), 7.73-7.69 (m, 3H), 7.49 (d, 1H), 7.39 (d, 1H), 7.33 (t, 1H), 7.14 (d, 2H), 4.95 (s, 2H), 4.26 (q, 2H), 2.98 (s, 3H), 2.51 (s, 3H), 1.29 (t, 3H).

ii) 2-methyl-3-[[4-(methylsulfonyl)phenyl]thio]-5-(3-pyridinyl)-1H-indole-1-acetic acid The title compound was prepared by the method of Example 1 part (v) using the product from part (ii). The basic solution was adjusted to pH5 with 0.5M hydrochloric acid and the resulting precipitate filtered off and dried to give the title compound (20 mg).

¹H NMR (DMSO-d6) δ 8.84 (d, 1H), 8.5 (dd, 1H), 8.1 (m, 1H), 7.73-7.69 (d, 3H), 7.63 (d, 1H), 7.53 (dd, 1H), 7.43 (dd, 1H), 7.18 (d, 2H), 5.22 (s, 2H), 3.12 (s, 3H) 2.44 (s, 3H) APCI+ [M+H] 453

EXAMPLE 36

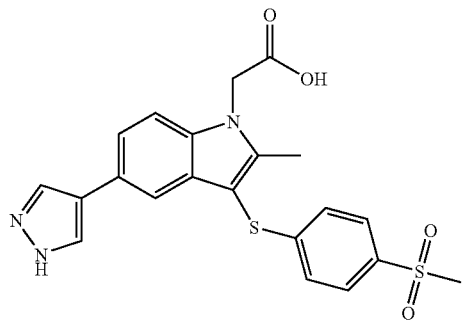

2-Methyl-3-[[4-(methylsulfonyl)phenyl]thio]-5-(1H-pyrazol-4-yl)-1H-indole-1-acetic acid i) 2-methyl-3-[[4-(methylsulfonyl)phenyl]thio]-5-(1H-pyrazol-4-yl)-1H-indole-1-acetic acid ethyl ester The sub-title compound was prepared by the method of Example 3 part (iii) using the product of part (ii) and (1H-pyrazol-4-yl)-boronic acid and used in the next step without characterisation.

ii) 2-methyl-3-[[4-(methylsulfonyl)phenyl]thio]-5-(1H-pyrazol-4-yl)-1H-indole-1-acetic acid The title compound was prepared by the method of Example 1 part (v) using the product from part (ii). The basic solution was adjusted to pH5 with 0.5M hydrochloric acid and the resulting precipitate filtered off and dried to give the title compound.

¹H NMR (DMSO-d6) δ 7.97 (s, 2H), 7.71 (d, 2H), 7.56 (d, 1H), 7.53 (s, 1H), 7.45 (dd, 1H), 7.16 (d, 2H), 5.14 (s, 2H), 3.12 (s, 3H) 2.4 (s, 3H) APCI+ [M+H] 442

EXAMPLE 37

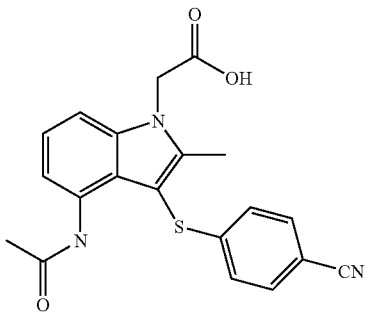

4-(Acetylamino)-3-[(4-cyanophenyl)thio]-2-methyl-1H-indole-1-acetic acid i) 4-(acetylamino)-3-[(4-cyanophenyl)thio]-2-methyl-1H-indole-1-acetic acid, ethyl ester The sub-title compound was prepared by the method of Example 5 part (iv) using the product from Example 13 part (i) (330 mg) and 4-mercaptobenzonitrile (330 mg). Purified using column chromatography (3% EtOAc/dichloromethane as eluent) to give the sub-title compound (300 mg).

$^1$H NMR (DMSO-d6) δ 9.33 (s, 1H), 8.07 (d, 1H), 7.47 (d, 2H), 7.23 (t, 1H), 7.09 (d, 2H), 7.02 (d, 1H), 4.88 (s, 2H), 4.23 (q, 2H), 2.44 (s, 3H), 1.93 (s, 3H), 1.28 (t, 3H) APCI+ [M+H] 408 M.p. 263-5° C.

ii) 4-(acetylamino)-3-[(4-cyanophenyl)thio]-2-methyl-1H-indole-1-acetic acid

The title compound was prepared by the method of Example 1 part (v) using the product from part (ii). The basic solution was adjusted to pH5 with 0.5M hydrochloric acid and the resulting precipitate filtered, dried to give the title compound.

$^1$H NMR (DMSO-d6) δ 7.63 (d, 2H), 7.37 (d, 1H), 7.27 (d, 1H), 7.13 (t, 1H), 7.07 (d, 2H), 5.13 (s, 2H), 2.37 (s, 3H) 1.79 (s, 3H) APCI+ [M+H] 380

Pharmacological Data

Ligand Binding Assay

[$^3$H]PGD$_2$ was purchased from Perkin Elmer Life Sciences with a specific activity of 100-210 Ci/mmol. All other chemicals were of analytical grade.

HEK cells expressing rhCRTh2/Gα16 were routinely maintained in DMEM containing 10% Foetal Bovine Serum (HyClone), 1 mg/ml geneticin, 2 mM L-glutamine and 1% non-essential amino acids. For the preparation of membranes, the adherent transfected HEK cells were grown to confluence in two layer tissue culture factories (Fisher, catalogue number TKT-170-070E). Maximal levels of receptor expression were induced by addition of 500 mM sodium butyrate for the last 18 hours of culture. The adherent cells were washed once with phosphate buffered saline (PBS, 50 ml per cell factory) and detached by the addition of 50 ml per cell factory of ice-cold membrane homogenisation buffer [20 mM HEPES (pH 7.4), 0.1 mM dithiothreitol, 1 mM EDTA, 0.1 mM phenyl methyl sulphonyl fluoride and 100 µg/ml bacitracin]. Cells were pelleted by centrifugation at 220×g for 10 minutes at 4° C., re-suspended in half the original volume of fresh membrane homogenisation buffer and disrupted using a Polytron homogeniser for 2×20 second bursts keeping the tube in ice at all times. Unbroken cells were removed by centrifugation at 220×g for 10 minutes at 4° C. and the membrane fraction pelleted by centrifugation at 90000×g for 30 minutes at 4° C. The final pellet was re-suspended in 4 ml of membrane homogenisation buffer per cell factory used and the protein content determined. Membranes were stored at −80° C. in suitable aliquots.

All assays were performed in Corning clear bottomed, white 96-well NBS plates (Fisher). Prior to assay, the HEK cells membranes containing CRTh2 were coated onto SPA PVT WGA beads (Amersham). For coating membranes were incubated with beads at typically 25 µg membrane protein per mg beads at 4° C. with constant agitation overnight. (The optimum coating concentrations were determined for each batch of membranes) The beads were pelleted by centrifugation (800×g for 7 minutes at 4° C.), washed once with assay buffer (50 mM HEPES pH 7.4 containing 5 mM magnesium chloride) and finally re-suspended in assay buffer at a bead concentration of 10 mg/ml.

Each assay contained 20 µl of 6.25 nM [$^3$H]PGD$_2$, 20 µl membrane saturated SPA beads both in assay buffer and 10 µl of compound solution or 13,14-dihydro-15-keto prostaglandin D$_2$ (DK-PGD$_2$, for determination of non-specific binding, Cayman chemical company). Compounds and DK-PGD$_2$ were dissolved in DMSO and diluted in the same solvent to 100× the required final concentration. Assay buffer was added to give a final concentration of 10% DMSO (compounds were now at 10× the required final concentration) and this was the solution added to the assay plate. The assay plate was incubated at room temperature for 2 hours and counted on a Wallac Microbeta liquid scintillation counter (1 minute per well).

Compounds of formula (I) have an IC$_{50}$ value of less than (<) 10 µM.

Specifically, example 14 has a pIC$_{50}$=6.65, example 26 has a pIC$_{50}$=8.35, and example 34 has a pIC$_{50}$=9.4.

The invention claimed is:

1. A compound having the formula:

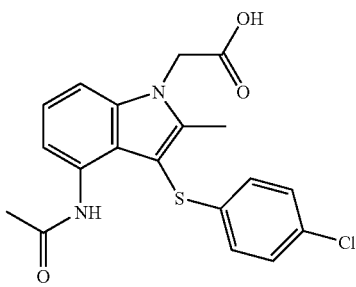

or a pharmaceutically acceptable salt thereof.

2. The compound or salt of claim 1, wherein the pharmaceutically acceptable salt is an ammonium salt, a sodium salt, a potassium salt, a calcium salt, an aluminium salt, a lithium salt, a magnesium salt, a zinc salt, a benzathine salt, a chloroprocaine salt, a choline salt, a diethanolamine salt, an ethanolamine salt, an ethyldiamine salt, a meglumine salt, a tromethamine salt, a procaine salt, a hydrochloride salt, a hydrobromide salt, a phosphate salt, an acetate salt, a fumarate salt, a maleate salt, a tartrate salt, a citrate salt, an oxalate salt, a methanesulphonate salt, or a p-toluenesulphonate salt.

3. The compound or salt of claim 1, wherein the pharmaceutically acceptable salt is a sodium salt or an ammonium salt.

4. A method of treatment of a respiratory disease mediated by CRTh2, which comprises administering to a patient a therapeutically effective amount of a compound or a pharmaceutically acceptable salt as claimed in claim 1.

5. The method of claim 4, wherein the disease is asthma.

6. The method of claim 4, wherein the disease is COPD.

7. A pharmaceutical composition comprising a compound or a pharmaceutically acceptable salt as claimed in claim 1 in association with a pharmaceutically acceptable adjuvant, diluent or carrier.

* * * * *